United States Patent [19]

Ishikawa et al.

[11] 4,405,623

[45] Sep. 20, 1983

[54] QUINAZOLINDE-DIONE COMPOUNDS, PROCESS FOR PRODUCTION THEREOF AND PHARMACEUTICAL USE THEREOF

[75] Inventors: Masayuki Ishikawa, 14-13, Akazutsumi 3-chome, Setagaya-ku, Tokyo; Akiko Sugimoto, Hino; Yukuo Eguchi, Chiba; Fujinori Sasaki, Yokohama; Hisashi Ebisawa, Chofu; Soyao Moriguchi; Katsuhiko Gotoh, both of Yokohama, all of Japan

[73] Assignee: Masayuki Ishikawa, Tokyo, Japan

[21] Appl. No.: 263,898

[22] Filed: May 15, 1981

[30] Foreign Application Priority Data

| May 15, 1980 | [JP] | Japan | 55/63328 |
| May 22, 1980 | [JP] | Japan | 55/67085 |
| Jun. 17, 1980 | [JP] | Japan | 55/80843 |
| Jun. 30, 1980 | [JP] | Japan | 55/87715 |
| Jul. 28, 1980 | [JP] | Japan | 55/102396 |
| Jul. 28, 1980 | [JP] | Japan | 55/102397 |
| Aug. 5, 1980 | [JP] | Japan | 55/106748 |
| Aug. 11, 1980 | [JP] | Japan | 55/109212 |

[51] Int. Cl.³ ............... C07D 239/80; A61K 31/505
[52] U.S. Cl. .................... 424/251; 424/248.55; 260/243.3; 544/116; 544/119; 544/284; 544/285

[58] Field of Search ............... 544/285, 116, 119, 284; 424/251, 248.55; 260/243.3

[56] References Cited

U.S. PATENT DOCUMENTS 3,882,121 5/1975 Cohen et al. .................. 544/285
4,276,295 6/1981 Ishikawa et al. .................. 424/251

*Primary Examiner*—Mark L. Berch
*Assistant Examiner*—James H. Turnipseed
*Attorney, Agent, or Firm*—Sherman & Shalloway

[57] ABSTRACT

A 5,6,7-substituted-2,4(1H,3H)-quinazolinedione compound of the formula (I),

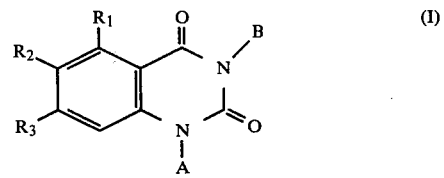

wherein $R_1$, $R_2$, $R_3$, A and B are as defined in claim 1 and its acid addition salt; and a vasodilating and hypotensive composition containing the aforesaid compound.

14 Claims, No Drawings

QUINAZOLINDE-DIONE COMPOUNDS, PROCESS FOR PRODUCTION THEREOF AND PHARMACEUTICAL USE THEREOF

This invention relates to novel 5,6,7-substituted-2,4(1H,3H)-quinazoline-dione compounds useful as vasodilators, hypotensive and antiatherosclerotic agents for the treatment of ischemic heart diseases, ischemic cerebral diseases, and hypertension.

More specifically, this invention relates to 5,6,7-substituted-2,4(1H,3H)-quinazoline-dione compound of the following formula (I),

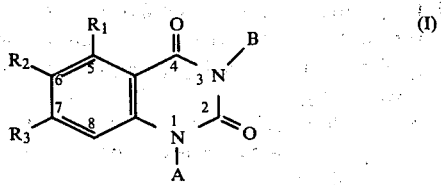

wherein
$R_1$ and $R_3$ independently represent (lower)alkyl groups;
$R_2$ represents a (lower)alkoxycarbonyl group;
B represents a (lower)alkyl group, a phenyl group or a substituted phenyl group substituted by at least one member selected from the group consisting of halogen atoms, (lower)alkyl groups, (lower)alkoxy groups, di(lower)alkylamino groups, a methylenedioxy group, a trifluoromethyl group, and a nitro group; and
A represents a member selected from the group consisting of a hydrogen atom, (lower)alkyl groups, carboxy(lower)alkyl groups, (lower)alkoxycarbonyl(lower)alkyl groups, hydroxy(lower)alkyl groups, a benzyl group and substituted benzyl groups which may be substituted by a nitro group or (lower)alkoxy group, pyridylmethyl groups, di-substituted-amino(lower)alkyl groups substituted by (lower)alkyl groups, a (lower)alkyl group and a benzyl group, a tetramethylene group, a pentamethylene group which may be substituted by (lower)alkyl groups, a hexamethylene group or a heptamethylene group, said methylene groups forming a heterocycle together with the nitrogen atom of the amino(lower)alkyl groups, (lower)alkyl groups bearing a piperidine or pyrrolidine ring, the nitrogen atom of which is substituted by a (lower)alkyl group, a moiety of the formula

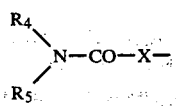

wherein X represents a (lower)alkylene group, $R_4$ represents a hydrogen atom or a (lower)alkyl group, $R_5$ represents a hydrogen atom, a (lower)alkyl, di(lower)alkylamino(lower)alkyl, benzyl, piperidino(lower)alkyl, morpholino(lower)alkyl, (1-piperazinyl) (lower)alkyl, [4-(lower)acyl-1-piperazinyl](lower)alkyl, or [4-carbamoyl-1-piperazinyl](lower)alkyl group, the carbamoyl group of which may be N-mono- or disubstituted by a (lower)alkyl or phenyl group, and $R_4$ and $R_5$ can form together with the nitrogen atom a piperidine or 4-(lower)alkylpiperazine ring,
a moiety of the formula

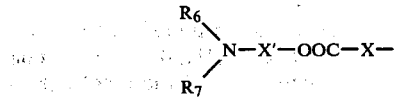

wherein $X'$ and X represent independently (lower)alkylene groups, $R_6$ represents a (lower)alkyl group, $R_7$ represents a (lower)alkyl, benzyl, piperidino(lower)alkyl, or morpholino(lower)alkyl group, and $R_6$ and $R_6$ can form together with the nitrogen atom a piperidine ring,
a moiety of the formula

wherein X represents a (lower)alkylene group, Y represents a nitrogen atom or a methine group, $R_8$ represents a hydrogen atom, a (lower)alkyl, phenyl, phenyl(lower)alkyl, or phenyl(lower)alkene group, the phenyl groups of which may be mono- or disubstituted by a chlorine atom or a methoxy group, a benzoyl group which may be substituted by a halogen atom, a nitro group, or a methoxy group, a phenylacetyl, benzyloxycarbonyl, cinnamoyl, thenoyl, furoyl, or N-phenylcarbamoyl group, provided that when Y is a methine group, $R_8$ is not hydrogen nor alkyl,
and a moiety of formula

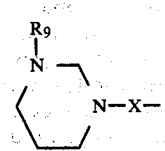

wherein X represents a (lower)alkylene group, and $R_9$ represents a phenyl or benzyl group,
and an acid addition salt thereof.

Heretofore, 7-alkoxycarbonyl-6,8-dialkyl-4-hydroxymethyl-1-phthalazinone derivative have been known as compounds which exhibit pharmacological properties such as the ability to prevent thrombosis and atherosclerosis (U.S. Pat. No. 3,963,716). Recently, 6-alkoxycarbonyl-5,7-dialkyl-4(3H)-quinazolinone derivatives bearing an aromatic moiety at the 3 position have been known to exhibit vasodilating, hypotensive and antiatherosclerotic activities (U.S. Pat. No. 4,276,295).

The present inventors have now found that the 5,6,7-substituted-2,4(1H,3H)-quinazolinedione compounds of formula (I) and the acid addition salts thereof which are not described in the literature can be easily synthesized, and have superior pharmacological activities as vasodilating and hypotensive agents to the prior art compounds described above. It has now been found that the compounds of the present invention have an efficient vasodilating effect on blood vessels such as coronary artery and cerebral artery. The vasodilating activities of the compounds of the present invention are approximately ten times as potent as the 4(3H)-quinazolinone derivative described above. The compounds of the invention are thus highly desirable as pharmaceutical agents for use in the treatment of ischemic diseases such as angina pectoris, heart infarction, cerebral infarction and hypertensive diseases.

It is an object of this invention therefore to provide the novel 5,6,7-substituted-2,4(1H,3H)-quinazolinedione compounds of formula (I) and the acid addition salts thereof.

Another object of this invention is to provide a vasodilating and hypotensive agent comprising the compound of formula (I) as an active ingredient, which is useful for the treatment of ischemic disorders, hypertension and the like.

Still another object of this invention is to provide a process for producing the compounds of formula (I).

The above and other objects and advantages of this invention will become more apparent from the following description.

The compounds of this invention are expressed by the following formula

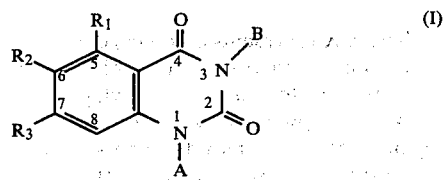

In formula (I), $R_1$ and $R_3$ represent a lower alkyl group, preferably a $C_1$-$C_3$ alkyl group such as a methyl, ethyl and propyl group, and $R_2$ represents a lower alkoxycarbonyl group, preferably an alkoxycarbonyl group having a $C_1$-$C_4$ alkoxy group which may be linear or branched, such as methoxy, ethoxy, propoxy, isopropoxy, n-butoxy or isobutoxy group.

In formula (I), B represents a lower alkyl group, a phenyl group or a substituted phenyl group substituted by at least one member selected from the group consisting of halogen atoms such as chlorine, bromine and fluorine atom, lower alkyl groups, preferably $C_1$-$C_3$ alkyl groups, as exemplified in $R_1$ and $R_3$, lower alkoxy groups, preferably $C_1$-$C_4$ alkoxy groups, as exemplified in $R_2$, di-lower-alkyl-amino groups, preferably having $C_1$-$C_3$ alkyl groups, as exemplified in $R_1$ and $R_3$, a methylenedioxy group, a trifluoromethyl group and a nitro group.

A in formula (I) represents a member selected from the group consisting of a hydrogen atom, lower alkyl groups, preferably ($C_1$-$C_4$)alkyl groups, carboxy-lower-alkyl groups, preferably carboxy ($C_1$-$C_4$)alkyl groups, lower alkoxycarbonyl-lower-alkyl groups, preferably ($C_1$-$C_4$)alkoxycarbonyl($C_1$-$C_4$)alkyl groups, hydroxy-lower-alkyl groups, preferably hydroxy($C_1$-$C_4$)alkyl groups, a benzyl group and substituted benzyl groups substituted by a nitro group or lower alkoxy group, preferably ($C_1$-$C_4$)alkoxy group, pyridylmethyl, disubstituted amino(lower)alkyl groups, disubstituted by lower alkyl groups, preferably ($C_1$-$C_4$)alkyl groups, or by a lower alkyl group, preferably ($C_1$-$C_4$)alkyl group, and a benzyl group, a tetramethylene group, pentamethylene groups which may be mono- and disubstituted by a lower alkyl group, preferably ($C_1$-$C_3$)alkyl group, a hexamethylene group, and a heptamethylene group, said methylene groups forming a heterocyclic together with the nitrogen atom of the amino(lower)alkyl groups, and lower alkyl groups, preferably ($C_1$-$C_4$)alkyl group which bear a piperidine or pyrrolidine ring, the nitrogen of which is substituted by a lower alkyl group, preferably ($C_1$-$C_4$)alkyl group.

a moiety of formula

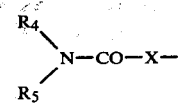

wherein X represents a lower alkylene group, preferably ($C_1$-$C_4$)alkylene group, which may be linear or branched such as methylene, ethylene, propylene, tetramethylene and 2-methylpropylene group, $R_4$ represents a hydrogen atom or a lower alkyl group, preferably ($C_1$-$C_4$)alkyl group, $R_5$ represents a hydrogen atom, a lower alkyl group, preferably ($C_1$-$C_3$)alkyl group, disubstituted-amino-lower alkyl group substituted by preferably ($C_1$-$C_3$)alkyl groups, a benzyl, piperidino-lower alkyl, preferably ($C_1$-$C_4$)alkyl group, morpholino-lower-alkyl, preferably ($C_1$-$C_4$)alkyl group, (1-piperazinyl)-lower-alkyl, preferably ($C_1$-$C_4$)alkyl group, [4-lower acyl-1-piperazinyl]-lower alkyl group, in which said acyl group is a ($C_1$-$C_4$)-acyl group such as acetyl, propionyl, and butyryl group and the alkyl group is a ($C_1$-$C_4$)alkyl group, and $R_4$ and $R_5$ can form together with the nitrogen atom a piperidine or 4-(lower)alkylpiperazine ring, preferably 4-($C_1$-$C_3$)-alkyl-piperazine ring, a moiety of formula

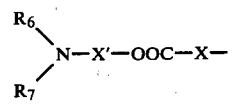

wherein X' and X, independently from each other, represent a (lower)alkylene group, preferably a ($C_1$-$C_4$)alkylene group as exemplified above, $R_6$ represents a (lower)alkyl, preferably ($C_1$-$C_3$)alkyl group, $R_7$ represents a (lower)alkyl, preferably a ($C_1$-$C_4$)alkyl group, or morpholino (lower)alkyl, preferably morpholino ($C_1$-$C_4$)alkyl group, and $R_6$ and $R_7$ can form together with the nitrogen atom a piperidine ring, a moiety of formula

wherein X represents a (lower)alkylene group, preferably ($C_1$-$C_4$)alkylene group as exemplified above, Y represents a nitrogen atom or a methine group, $R_8$ represents a hydrogen atom, a (lower)alkyl, preferably ($C_1$-$C_4$)-alkyl group, a phenyl, phenyl(lower)alkyl (preferably $C_1$-$C_4$ alkyl), or phenyl(lower)alkene (preferably $C_1$-$C_4$ alkene group), the phenyl groups of which may be mono- or di-substituted by a chlorine atom or a methoxy group, a benzoyl group which may be substituted by a halogen atom or a methoxy group, a phenylacetyl, benzyloxycarbonyl, cinnamoyl, thenoyl, furoyl, or N-phenylcarbamoyl group, provided that when Y is a methine group, $R_8$ is not hydrogen nor alkyl, and a moiety of formula

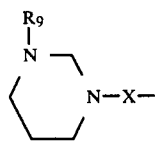

wherein X represents a (lower)alkylene group, preferably a ($C_1$-$C_4$)alkylene group as exemplified above, and $R_9$ represents a phenyl or benzyl group.

The compound of formula (I) in which A is a hydrogen atom, expressed by the following formula

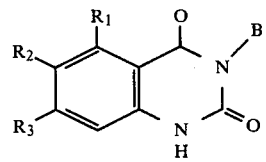 (I')

wherein $R_1$, $R_2$, $R_3$ and B are as defined above with regard to formula (I), can be produced by reacting a compound of the following formula

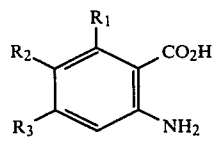 (II)

wherein $R_1$, $R_2$ and $R_3$ are as defined above with regard to formula (I), with a compound of the following formula

 (III)

wherein B is as defined above with regard to formula (I), and thereafter treating the product in an acidic medium.

The compound of formula (I) in which A is not a hydrogen atom, expressed by the following formula

 (I'')

wherein $R_1$, $R_2$, $R_3$ and B are as defined above with regard to formula (I), and
A is as defined above with regard to formula (I), excluding a hydrogen atom, can be produced by reacting a compound of the formula (I') with a compound of the following formula A—Hal (IV)

wherein A is as defined above with regard to formula (I), excluding a hydrogen atom, and Hal represents a chlorine, bromine or iodine atom,
and if desired, treating the product with an acid, preferably a pharmaceutically acceptable acid to convert it into an acid addition salt.

Alternatively, the compound of formula (I') can be produced by reacting a compound of formula (II) with thionyl chloride, and then reacting the product with a compound of the following formula

B—$NH_2$ (V)

wherein B is as defined with regard to formula (I), and thereafter reacting the product with phosgene or a compound of the following formula ClCOO—(lower)alkyl (VI)

wherein (lower)alkyl represents a methyl or ethyl group.

Furthermore, the compound of formula (I'') and its acid addition salts can be produced alternatively by reacting a compound of formula (II) with a compound of formula (IV), and then reacting the product with a compound of formula (III), and thereafter treating the product in an acidic medium, and if desired, treating the product with an acid, preferably a pharmaceutically acceptable acid to convert it into an acid addition salt.

The processes of the present invention described above can be schematically shown as follows:

Scheme 1

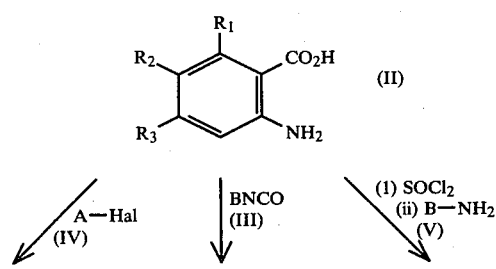

Scheme 1 -continued

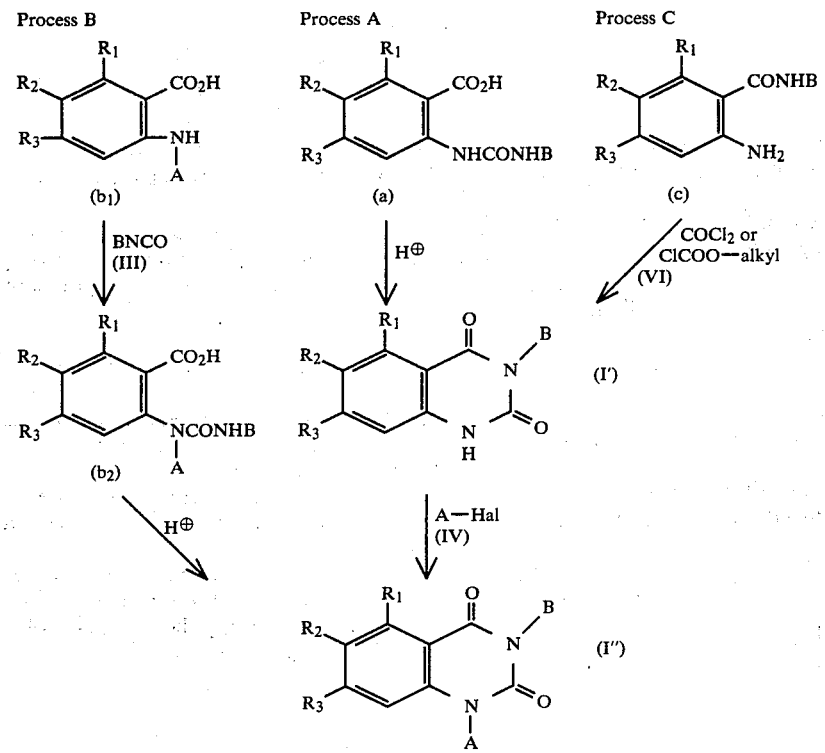

Specific embodiments of processes A to D are described in detail below.

Examples of the starting compound of formula (II) are 2-amino-5-ethoxycarbonyl-4,6-dimethylbenzoic acid, 2-amino-4,6-dimethyl-5-propoxycarbonylbenzoic acid, 2-amino-5-isopropoxycarbonyl-4,6-dimethylbenzoic acid, 2-amino-5-butoxycarbonyl-4,6-dimethylbenzoic acid, and 2-amino 5-isobutoxycarbonyl-4,6-dimethylbenzoic acid.

The compound of formula (II) can be produced by known means, for example by the Hoffmann rearrangement reaction of a 4-alkoxycarbonyl-3,5-dialkylphthalimide (see Eguchi and Ishikawa, Report of Institute for Medical and Dental Engineering, Tokyo Medical and Dental University, Vol. 11, page 55, 1977), or the Curtius rearrangement reaction of a 2,4-dialkoxycarbonyl-3,5-dialkylbenzoic acid azide.

Examples of the compound of formula (III) in processes A and B include phenyl isocyanate, o-, m-, and p-chlorophenyl isocyanates, o-, m-, and p-bromophenyl isocyanates, o-, m-, and p-fluorophenyl isocyanates, o-, m-, and p-tolyl isocyanates, o-, m-, and p-methoxyphenyl isocyanates, 3,4-dimethoxyphenyl isocyanate, 3,4-methylenedioxyphenyl isocyanate, α,α,α-trifluoro-o-, -m-, and -p-tolyl isocyanates, o-, m-, and p-nitrophenyl isocyanates, o-, m-, and p-(N,N-dimethylamino)phenyl isocyanates, o-, m-, and p-(N,N-diethylamino)phenyl isocyanates, o-, m-, and p-(N,N-diethylamino)phenyl isocyanates, 2,4-dichlorophenyl isocyanate, 2,6-dichlorophenyl isocyanate, 2,3-, 2,4-, 2,5-, 2,6-dimethylphenyl isocyanates, 3-chloro-2-methylphenyl isocyanate, 4-chloro-2-methylphenyl isocyanate, 5-chloro-2-methoxyphenyl isocyanate, 3-chloro-4-methylphenyl isocyanate, 4-methoxy-2-nitrophenyl isocyanate, 2-methoxy-4-nitrophenyl isocyanate, 2-methoxy-5-nitrophenyl isocyanate, 2-bromo-4-methylphenyl isocyanate, 4-(N,N-diethylamino)-2-methoxyphenyl isocyanate, 2-chloro-4-(trifluoromethyl)phenyl isocyanate, 4-chloro-2-(trifluoromethyl)phenyl isocyanate, and 2-nitro-4-(trifluoromethyl)phenyl isocyanate.

Examples of the compound of formula (IV) in processes A and B include methyl iodide, ethyl iodide, propyl bromide, isopropyl bromide, 1-chlorobutane, 2-chlorobutane, 1-chloro-2-methylpropane, 1-bromo-3-methylbutane, 1-bromopentane, 2-bromopentane, 1-bromo-3-methylbutane, esters of chloroacetic acid such as ethyl-, propyl-, isopropyl-, and t-butyl chloroacetates, esters of 3-chloropropionic acid such as methyl-, ethyl-, propyl-, isopropyl-, and t-butyl 3-chloropropionates, esters of 2-bromopropionic acid such as methyl-, ethyl-, propyl- and t-butyl 2-bromopropionates, esters of 4-chlorobutylic acid such as methyl-, ethyl- and propyl 4-chlorobutylates, 2-(N,N-dimethylamino)ethyl chloride, 2-(N,N-diethylamino)ethyl chloride, 2-(N,N-dipropylamino)ethyl chloride, 3-(N,N-diethylamino)propyl chloride, 3-(N,N-dimethylamino)propyl chloride, 2-(N,N-dimethylamino)propyl chloride, 4-(N,N-dimethylamino)-butyl chloride, 4-(N,N-diethylamino)-butyl chloride, 3-(N,N-dimethylamino)-2-methylpropyl chloride, 3-(N,N-diethylamino)-2-methylpropyl chloride, 2-(N-ethyl-N-methylamino)ethyl chloride, N-(2-chloroethyl)pyrrolidine, N-(2-chloroethyl)piperidine, N-(3-chloropropyl)piperidine, N-(3-chloropropyl)pyrrolidine, 4-(2-chloroethyl)morpholine, 4-(3-chloropropyl)morpholine, N-(4-chlorobutyl)pyrrolidine, N-(4-chlorobutyl)piperidine, 4-(4-chlorobutyl)morpholine, 2-chloroacetamide, N-methyl-2-chloroacetamide, N-ethyl-2-chloroacetamide, N-propyl-2-chloroacetamide, N-isopropyl-2-chloroacetamide, N,N-dimethyl-2- chloroacetamide, N,N-diethyl-2-chloroacetamide, N-benzyl-2-chloroacetamide, N-benzyl-N-methyl-2-chloroacetamide, N-benzyl-N-ethyl-2-chloroacetamide, N-(2-dimethylaminoethyl)-2-chloroacetamide, N-(2-diethylaminoethyl)-2-chloroacetamide, N-(3-dimethylaminopropyl)-2-chloroacetamide, N-(3-diethylaminopropyl)-2-chloro acetamide, N-(chloroacetyl)pyrrolidine, N-(3-chloropropionyl)pyrrolidine, N-(chloroacetyl)piperidine, N-(3-chloropropionyl)piperidine, N-(4-chlorobutryl)-piperidine, 4-(chloroacetyl)morpholine, 4-(4-chlorobutyryl)morpholine, 1-chloroacetyl-4-methylpiperazine, 1-chloroacetyl-4-ethylpiperazine, 1-(3-chloropropionyl)-4-methylpiperazine, N-[2-(chloroacetylamino)ethyl]pyrrolidine, N-[3-(chloroacetylamino)propyl]pyrrolidine, N-[2-(chloroacetylamino)ethyl]piperidine, N-[3-(chloroacetylamino)propyl]piperidine, N-[4-chloroacetylamino)-butyl]piperidine, 1-[2-(chloroacetylamino)ethyl]-4-methylpiperazine, [3-chloroacetylamino)propyl]-4-methylpiperazine, 4-[2-(chloroacetylamino)ethyl]morpholine, 2-(N-benzyl-N-methylamino)ethyl chloride, 2-(N-benzyl-N-ethylamino)ethyl chloride, 2-(N-benzyl-N-propylamino)-ethyl chloride, 3-(N-benzyl-N-methylamino)propyl chloride, 3-(N-benzyl-N-ethylamino)propyl chloride, 4-(N-benzyl-N-methylamino)butyl chloride, 2-(N,N-dimethylamino)ethyl chloroacetate, 2-(N,N-diethylamino)ethyl chloroacetate, 3-(N,N-dimethylamino)propyl chloroacetate, 3-(N,N-diethylamino)propyl chloroacetate, 4-(N,N-dimethylamino)butyl chloroacetate, 2-(N-benzyl-N-methylamino)ethyl chloroacetate, 3-(N-benzyl-N-methylamino)propyl chloroacetate, 4-(N-benzyl-N-methylamino)butyl chloroacetate, 2-piperidinoethyl chloroacetate, 3-piperidinopropyl chloroacetate, 2-(pyrrolidine-1-yl)ethyl chloroacetate, 3-(pyrrolidine-1-yl)propyl chloroacetate, 4-piperidinobutyl chloroacetate, 2-morpholinoethyl chloroacetate, 3-morpholinopropyl chloroacetate, 2-[1-(4-methylpiperazinyl)]ethyl chloroacetate, 3-[1-(4-methylpiperazinyl)] propyl chloroacetate, 2-piperidinoethyl 3-chloropropionate, 3-piperidinopropyl 3-chloropropionate, benzyl chloride, o-, m- and p-chlorobenzyl chlorides, o-, m- and p-nitrobenzyl chlorides, o-, m- and p-methoxybenzyl chlorides, 3,4-dimethoxybenzyl chloride, 3,4,5-trimethoxybenzyl chloride, 2-(2-chloroethyl)-N-methylpyrrolidine, 2-(2-chloroethyl)-N-ethylpyrrolidine, 2-(3-chloropropyl)-N-methylpyrrolidine, 2-(3-chloropropyl)-N-ethylpyrrolidine, 3-chloromethyl-N-methylpiperidine, 3-chloromethyl-N-ethylpiperidine, 3-(2-chloroethyl)-N-methylpiperidine, 3-(2-chloroethyl)-N-ethylpiperidine, 2-(2-chloroethyl)-N-benzylpyrrolidine, 2-pyridylmethyl chloride, 3-pyridylmethyl chloride, 4-pyridylmethyl chloride, 2-(3-chloropropyl)-N-benzylpyrrolidine, 3-chloromethyl-N-benzylpiperidine, 3-(2-chloroethyl)-N-benzylpiperidine, 1-(2-chloroethyl)-4-methylpiperidine, 1-(3-chloropropyl)-4-methylpiperidine, 1-(2-chloroethyl)-4-phenylpiperidine, 1-(3-chloropropyl)-4-phenylpiperidine, 1-(2-chloroethyl)-4-(o-chlorophenyl)-piperidine, 1-(3-chloropropyl)-4-(o-chlorophenyl)-piperidine, 1-(2-chloroethyl)-4-(m-chlorophenyl)-piperidine, 1-(3-chloropropyl)-4-(m-chlorophenyl)-piperidine, 1-(2-chloroethyl)-4-(p-chlorophenyl)-piperidine, 1-(3-chloropropyl)-4-(p-chlorophenyl)-piperidine, 1-(2-chloroethyl)-4-(o-methoxyphenyl)-piperidine, 1-(3-chloropropyl)-4-(p-methoxyphenyl) piperidine, 1-(2-chloroethyl)-4-benzylpiperidine, 1-(3-chloropropyl)-4-benzylpiperidine, 1-(2-chloroethyl)-2,6-dimethylpiperidine, 1-(3-chloropropyl)-2,6-dimethylpiperidine, 2-(4-formyl-1-piperazinyl)ethyl chloride, 3-(4-formyl-1-piperazinyl)propyl chloride, 2-(4-acetylpiperazinyl)ethyl chloride, 3-(4-acetyl-1-piperazinyl) propyl chloride, 2-(4-propionyl-1-piperazinyl)ethyl chloride, 2-(4-butyryl-1-piperazinyl)ethyl chloride, 2-(4-isobutyryl-B 1-piperazinyl)ethyl chloride, 2-(4-carbamoyl-1-piperazinyl)ethyl chloride, 2-[4-(N-methyl) carbamoyl-1-piperazinyl]ethyl chloride, 3-[4-(N-ethyl) carbamoyl-1-piperazinyl]propyl chloride, 2-(4-benzoyl-1-piperazinyl)ethyl chloride, 2-[4-(o-, m- and p-chlorobenzoyl)-1-piperazinyl]ethyl chlorides, 2-[4-(o-, m- and p-methoxybenzoyl)-1-piperazinyl]ethyl chlorides, 2-[4-(3,4-dimethoxybenzoyl)-1-piperazinyl]ethyl chloride, 2-[4-(3,4,5-trimethoxybenzoyl)-1-piperazinyl]ethyl chloride, 2-(4-phenylacetyl-1-piperazinyl)ethyl chloride, 2-[4-cinnamoyl-1-piperazinyl]ethyl chloride, 2-[4-(3,4,5-trimethoxycinnamoyl)-1-piperazinyl]ethyl chloride, 2-(4-furoyl-1-piperazinyl)ethyl chloride, 2-(4-picolinoyl-, nicotinoyl- and isonicotinoyl-1-piperazinyl)ethyl chloride, 2-[4-(N-phenyl)carbamoyl-1-piperazinyl]ethyl chloride, 1-[2-(chloroacetylamino)ethyl]-4-acetylpiperazine, 1-[2-(chloroacetylamino)ethyl]-4-(N-methyl)carbamoylpiperazine, 1-[3-(chloroacetylamino)propyl]-4-acetylpiperazine, 1-[3-(chloroacetylamino)propyl]-4-(N-methyl)carbamoylpiperazine, 1-[2-(chloroacetylamino)ethyl]-4-(N-phenyl)carbamoyl chloride, 1-(2-chloroethyl)3-benzylhexahydropyrimidine, 1-(3-chloropropyl)-3-benzylhexahydropyrimidine, 1-(2-chloroethyl)-3-phenylhexahydropyrimidine, and 1-(3-chloropropyl)-3-phenylhexahydropyrimidine.

Examples of the compound of formula (V) in process C include aniline, o-, m-, and p-chloroanilines, o-, m-, and p-bromoanilines, o-, m-, and p-fluoroanilines, o-, m-, and p-toluidines, o-, m-, and p-anisidines, 3,4-dimethoxyaniline, 3,4-methylenedioxyaniline, α,α,α-trifluoro-o-, -m-, and -p-toluidines, o-, m-, and p-nitroanilines, N,N-dimethyl-o-, -m-, and -p-phenylenediamines, N,N-diethyl-o-, -m- and -p-phenylenediamines, 2,4-dichloroaniline, 2,6-dichloroaniline, 2,3-, 2,4-, 2,5-, and 2,6-xylenes, 2,4,6-trimethylaniline, 3-chloro-2-methylaniline, 4-chloro-2-methylaniline, 5-chloro-2-methoxyaniline, 3-chloro-4-methylaniline, 4-hydroxy-2-methylaniline, 2-amino-4-nitrophenol, 2-amino-5-nitrophenol, 2-amino-4-chlorophenol, 2-amino-4-methylphenol, 4-amino-2-nitrophenol, 4-methoxy-2-nitroaniline, 2-methoxy-4-nitroaniline, 2-methoxy-5-nitroaniline, 2-bromo-4-methylaniline, 4-diethylamino-2-methoxyaniline, 2-chloro-4-(trifluoromethyl)aniline, 4-chloro-2-(trifluoromethyl)aniline, and 2-nitro-4-(trifluoromethyl)aniline.

According to process A, the compound of formula (II) is reacted with an equimolar or slightly excessive amount of a compound of formula (III) in an inert organic solvent such as diethyl ether, dichloromethane, tetrahydrofuran or pyridine. The reaction proceeds at room temperature and ends within about 3 to 12 hours. After evaporation of the solvent, the resulting residue [compound (a) in scheme 1] is then treated with methanol or ethanol containing about 3 to 10% hydrogen chloride. The temperature and time of the ring-closure reaction can be selected properly, and may, for example, be about 50° to about 80° C. and about one to 3 hours, respectively. After evaporation of the solvent, the resulting residue is worked up in a customary manner to afford the compound of formula (I') in a theoretical yield of 60 to 85%, based on the compound of formula (II).

The compound of formula (I') produced by the above procedure can be converted to a compound of formula (I'') by the reaction with a compound of formula (IV) in the presence of an alkali metal hydride. The reaction of the compound of formula (I') and the compound of formula (IV) is carried out preferably in an inert organic solvent such as dimethyl formamide, dimethyl sulfoxide, N-methylpyrrolidone, and hexamethylphosphoramide. These solvents can be used, if desired, after being diluted with dichloromethane, toluene, or xylene. The amount of the solvent used in the reaction is not specially limited; it may, for example, be about 100 to 1000 times the volume of the compound of formula (I'). In an embodiment of the process, the compound of formula (I') is treated in a solvent described above with an equimolar or slightly excessive amount of an alkali metal hydride such as sodium hydride, preferably in the form of a fine suspension in a mineral oil, in order to replace the hydrogen atom at the 1-position of the compound of formula (I') with metal. For this purpose, sodium amide or n-butyl lithium can also be used. In order to accelerate the replacement, it is desirable to heat the mixture of the compound of formula (I') and sodium hydride at about 60° to 120° C. for about 30 minutes to one hour, prior to addition of compound of formula (IV). The preferred amount of the compound of formula (IV) is, for example, about 1 to 3 moles, specifically 1.2 to 1.5 moles per mole of the compound of formula (i'). The reaction temperature and time can be selected properly according to the reactivity of the compound of formula (IV). When the halogen atom of the compound (IV) is activated by a neighboring activating group such as a carbonyl group, the preferred reaction temperature may, for example, be about 60° to 80° C. Otherwise, reaction temperatures between about 120° to about 180° C., preferably between about 140° to about 150° C. are generally desirable, and the reaction time may be about 3 to 10 hours. The reaction mixture can be worked up in a conventional manner, for example, by extraction with an organic solvent, recrystallization, or chromatography over silica gel to afford the compound of formula (I'') in a yield of about 50 to 80%.

Alternatively, the compound of formula (I'') can be produced by process B, which involves the reaction of a compound of formula (II) with a compound of formula (IV). The process is performed, for example, as follows: A compound of formula (II) is stirred in a solvent such as water, methanol, or ethanol with a compound (IV) in the presence of a dehydrohalogenating agent. The amount of the compound (IV) can be suitably selected and may, for example, be about 1 to 3 moles per mole of the compound (II). A dehydrohalogenating agent such as sodium hydrogencarbonate or potassium carbonate is added to the reaction mixture in an amount of 5 to 20 moles per mole of the compound (IV). The reaction is carried out preferably at room temperature for about one to 3 days. Customary working up of the reaction mixture affords the product [the compound ($b_1$) in scheme 1] in a yield of 50 to 80% (of theory). Next, the above product is reacted with a compound of formula (III) in a similar manner to process A to afford the product [compound ($b_2$) in scheme 1]. Thereafter, the product is ring-closed, without isolation, to the compound of formula (I'') by the treatment in an acidic medium in a similar manner to process A in a yield of 50 to 80% (of theory).

Alternatively, the compound of formula (I') can be produced by process C, as illustrated below. A compound of formula (II) is refluxed with an excessive amount of thionyl chloride for about 30 minutes to one hour. After evaporation of the excess thionyl chloride, the residue is reacted with a compound of formula (V) in a solvent such as pyridine at room temperature. Working up of the reaction mixture in a customary manner gives the product [compound (c) in scheme 1] in a yield of 30 to 50% (of theory). The compound (c) is then dissolved in a solvent such as toluene, dichloromethane, or chloroform, and then treated with an equimolar or excessive amount of phosgene. After the reaction is allowed to proceed at room temperature for about 5 to 10 hours, a dehydrochlorinating agent such as pyridine or dimethylaniline is added, and the mixture is then refluxed for about 2 to 8 hours. Working up of the reaction mixture in a customary manner gives the compound of formula (I') in a yield of 40 to 60% (of theory). Alternatively, the above ring-closure reaction can be carried out in a similar yield by treating the compound (c) with an alkyl chloroformate such as methyl chloroformate or ethyl chloroformate in the presence of an excess of a sodium alkoxide such as sodium methoxide or sodium ethoxide. The reaction is preferably performed in a solvent such as methanol or ethanol.

Furthermore, the compounds of formula (II''), which carry at the $C_1$-side chain a functional group such as an ester group or an amino group protected by an amino-protecting group such as a benzyloxycarbonyl group, can be converted to another kind of the compounds (I'') by conventional synthetic procedures which are known by themselves. These processes are illustrated below by the following examples shown in schemes 2 and 3.

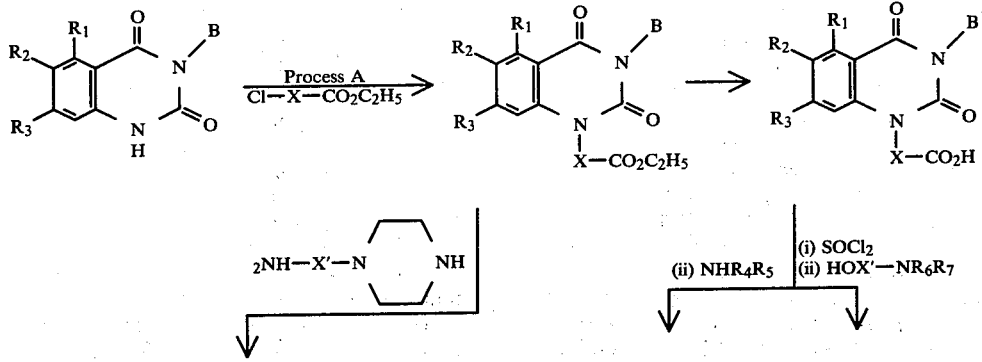

-continued
Scheme 2

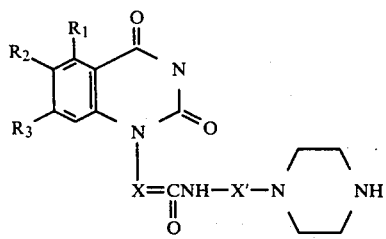 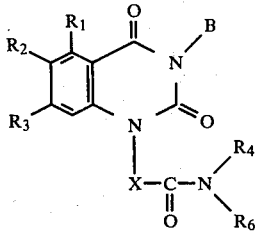 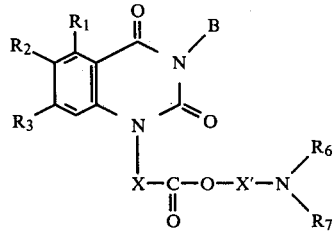

Scheme 3

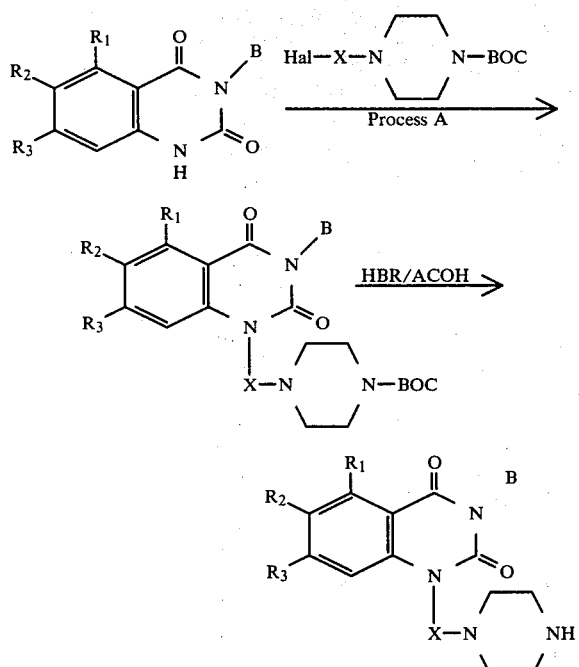

BOC = benzyloxycarbonyl group

In the above schemes 2 and 3, $R_1$, $R_2$, $R_3$, $R_4$, $R_5$, $R_6$, $R_7$, B, X, and X' are as defined above with regard to formula (I).

Thus, the above process is particularly advantageous for the production of the compounds of formula (I) bearing a piperazine ring at the side chain, in which one of the two nitrogen atoms has a free hydrogen atom.

If desired, the comound of formula (I) can be converted to its acid addition salt, preferably its pharmaceutically acceptable acid addition salt by conventional general procedures. Examples of acids that can be used to form such a salt include inorganic acids such as hydrochloric acid, sulfuric acid and hydrobromic acid, and organic acids such as oxalic acid, maleic acid, malic acid and tartaric acid.

According to this invention, there is provided a vasodilating, and hypotensive agent useful for the treatment of diseases caused by ischemic heart disorder, ischemic cerebral disorder, hypertension and the like, which comprises an effective amount of the 2,4(1H,3H)-quinazolinedione of formula (I) or its pharmaceutically acceptable acid addition salt, and a pharmaceutically acceptable liquid or solid diluent or carrier.

Examples of such pharmaceutically acceptable liquid or solid diluent or carrier include solid carriers such as sodium chloride, glucose, lactose, starch, sucrose, magnesium stearate, cetyl alcohol, cacao butter and spermaceti; and liquid carriers such as distilled water, isotonic sodium chloride solution, Ringer's solution, Locke's solution, polyethylene glycol, propylene glycol, ethyl alcohol, glycerol and vegetable oils.

The vasodilators of this invention may be in various formulations such as powders, granules, particles, tablets, capsules, troches, suspensions and solutions.

The dosage of the vasodilator of this invention is about 1 to about 100 mg/kg/day although it can be properly changed depending upon the type and extent of the patient's condition, the method of administration, etc.

The amount of the compound of formula (I) or its pharmaceutically acceptable acid addition salt to be included in the vasodilator of this invention can be properly changed according to the formulation of the vasodilator, the method of administration, etc. For example, it is about 1 to about 80% by weight based on the weight of the vasodilator.

Tests for pharmacological effects and for acute toxicity of several examples of the compounds of this invention are shown below under the headline "Test for blood vessel relaxing effect" and "Test for acute toxicity".

The following Examples illustrate the production of the compounds of this invention.

EXAMPLE 1

2-Chlorophenyl isocyanate (340 mg) was added to a stirred solution of 2-amino-5-ethoxycarbonyl-4,6-dimethylbenzoic acid (474 mg) in diethyl ether (20 ml) and the mixture was stirred for 12 hours at room temperature. After evaporating off the solvent, the residue was dissolved in ethanol (20 ml) containing 5% hydrogen chloride, and the solution was then refluxed for 3 hours. The solvent was evaporated off under reduced pressure, and the residue was chromatographed over a column of silica gel. The fractions obtained from the eluates with CHCl$_3$ were recrystallized from diethyl ether/n-hexane to give 6-ethoxycarbonyl-5,7-dimethyl-3-(2-chlorophenyl)-2,4-(1H,3H)-quinazolinedioxane melting at 233°–234° C. The total yield of the product was 84.4% (628 mg). MS: m/e, 372(M+), 337, 327, 309. NMR: δ(ppm, CDCl$_3$) 1.39 (3H, t), 2.29 (3H, s), 2.70 (3H, s), 4.35 (2H, q), 6.68 (1H, s), 7.20–7.50 (4H, m), 10.27 (1H, s).

EXAMPLE 2

α,α,α-Trifluoro-o-tolyl isocyanate (434 mg) was added to a solution of 2-amino-5-ethoxycarbonyl-4,6-dimethylbenzoic acid (500 mg) in diethyl ether (22 ml), and the mixture was stirred overnight. The resulting precipitate was filtered off and dissolved in ethanol (15 ml). Then, hydrogen chloride (1 g) was introduced into the solution. The reaction mixture was refluxed for 3 hours and the solvent was evaporated off. The residue was recrystallized from diethyl ether to give 6-ethoxycarbonyl-5,7-dimethyl-3-[2-(trifluoromethyl)phenyl]-2,4-(1H,3H)-quinazolinedione (575 mg, 67%) melting at 175°–176° C. MS: m/e, 406(M+), 377, 361, 357, 337, 332, 314, 309. NMR: δ(ppm, CDCl₃) 1.40 (3H, t), 2.30 (3H, s), 2.68 (3H, s), 4.44 (2H, q), 6.70 (1H, b), 7.2–8.0 (4H, m), 10.25 (1H, s).

EXAMPLES 3–20

In a similar manner to Examples 1 and 2, starting from 2-amino-5-ethoxycarbonyl-4,6-dimethylbenzoic acid, the following compounds of formula ($I_a$) were obtained in 60–85% yields as shown in Table I.

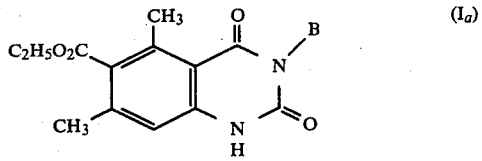

TABLE I

| No. | Compound of formula ($I_a$) B | Melting point (°C.) | Recrystallization solvent |
|---|---|---|---|
| 3 | phenyl | 288–290 | ethanol |
| 4 | o-fluorophenyl | 197–198 | ethanol/ether |
| 5 | o-tolyl | 210–211 | ether/n-hexane |
| 6 | m-tolyl | 283–284 | ethanol |
| 7 | p-tolyl | 267–268 | ethanol |
| 8 | m-chlorophenyl | 285–286 | ethanol |
| 9 | p-chlorophenyl | >300 | ethanol |
| 10 | m-methoxyphenyl | 254–255 | ethanol |
| 11 | p-methoxyphenyl | 263–264 | ethanol |
| 12 | o-nitrophenyl | 210–211 | ethanol/ether |
| 13 | m-nitrophenyl | 286–287 | ethanol |
| 14 | p-nitrophenyl | 288–289 | ethanol |
| 15 | m-(trifluoromethyl)phenyl | 244–246 | ethanol |
| 16 | 2,4-dichlorophenyl | 162–163 | ethanol-water |
| 17 | 2-bromo-4-methylphenyl | 224–225 | ethanol-water |
| 18 | 2-nitro-4-(trifluoromethyl)phenyl | 225–226 | ether |
| 19 | 3,4-(methylenedioxy)phenyl | 266–268 | CHCl₃/n-hexane |
| 20 | 2-methyl-4-(diethylamino)phenyl | hydrochloride: 186–188 (decomp.) | CHCl₃/ether |

EXAMPLE 21

A portion (96 mg) of sodium hydride suspension (50%) in mineral oil was added to a stirred solution of 3-(2-chlorophenyl)-6-ethoxycarbonyl-5,7-dimethyl-2,4-(1H, 3H)-quinazolidione (372 mg) in dimethylformamide (20 ml). After stirring the mixture for one hour at 100° C., 3-(N,N-dimethylamino)propyl chloride hydrochloride (158 mg) was added. The mixture was heated to 140°–150° C. and maintained at this temperature for 3 hours with stirring. The solvent was evaporated off and the residue was treated with CHCl₃. The CHCl₃ phase was washed with 10% aqueous K₂CO₃ solution, dried over anhydrous MgSO₄ and concentrated. The residue was chromatographed over a column of silica gel, and the fractions obtained from the eluates with CHCl₃-methanol (v/v, 9:1) were recrystallized from ethanol/diethyl ether to give 3-(2-chlorophenyl)-6-ethoxycarbonyl-5,7-dimethyl-[3-(N,N-dimethylamino)propyl]-2,4-(1H,3H)-quinazolinedione (320 mg, 70%) melting at 155°–156° C. MS: m/e, 457(M+), 412, 337. NMR: δ(ppm CDCl₃), 1.40 (3H, t), 1.75–2.60 (4H, m), 2.26 (6H, s), 2.43 (3H, s), 2.72 (3H, s), 4.25 (2H, t), 4.43 (2H, q), 7.13–7.60 (5H, m).

EXAMPLE 22

A portion (50 mg) of sodium hydride suspension (50%) in mineral oil was added to a stirred solution of 3-(2-chlorophenyl)-6-ethoxycarbonyl-5,7-dimethyl-2,4-(1H,3H)-quinazolinedione (373 mg) in dried dimethylformamide (20 ml). After addition of ethyl chloroacetate (123 mg), the mixture was stirred at 70° C. for one hour. The solvent was evaporated at reduced pressure, and the residue was extracted with CHCl₃, and the CHCl₃ extract was washed with water, dried over anhydrous MgSO₄ and concentrated. The residue was recrystallized from ethanol to give 3-(2-chlorophenyl)-1-ethoxycarbonylmethyl-6-ethoxycarbonyl-5,7-dimethyl-2,4(1H,3H)-quinazolinedione (287 mg, 62.6%) melting at 158°–159° C. MS: m/e, 458(M+), 423. NMR: δ (ppm, CDCl₃), 1.28 (3H, t), 1.39 (3H, t), 2.40 (3H, s), 2.74 (3H, s), 4.28 (2H, q), 4.42 (2H, q), 4.92 (2H, s), 6.74 (1H, s), 7.41 (4H, m).

EXAMPLE 23

A portion (30 mg) of sodium hydride suspension (50%) in mineral oil was added to a stirred solution of 3-(2-chlorophenyl)-6-ethoxycarbonyl-5,7-dimethyl-2,4-(1H, 3H)-quinazolinedione (187 mg) in dimethylformamide (10 ml). After addition of N,N-diethylchloroacetamide (80 mg), the mixture was stirred at 80° C. for 3 hours. The solvent was evaporated off at reduced pressure, and the residue was extracted with CHCl₃. The CHCl₃ extract was washed with water, dried over NaSO₄ and concentrated. The residue was recrystallized from methanol to give 3-(2-chlorophenyl)-6-ethoxycarbonyl-5,7-dimethyl-1-(N,N-diethyl)aminocarbonylmethyl-2,4(1H, 3H)-quinazolinedione (138 mg, 57%) melting at 228°–229° C. MS: M/e, 485(M+), 450. NMR: δ (ppm, CDCl₃), 1.38 (9H, m), 2.39 (3H, s), 2.72 (3H, s), 3.45 (4H, q), 4.40 (2H, q), 4.95 (2H, d), 6.75 (1H, s), 7.40 (4H, m).

EXAMPLE 24

A portion (96 mg) of 50% sodium hydride suspension in mineral oil was added to a solution of 3-(2-chlorophenyl)-6-ethoxycarbonyl-5,7-dimethyl-2,4(1H, 3H)-quinazolinedione (372 mg) in dimethylformamide (20 ml). After stirring the mixture at 100° C. for one hour, 3-(N-benzyl-N-methylamino)propyl chloride hydrochloride (320 mg) was added. The mixture was heated to 140°–145° C. and maintained at this temperature for 6 hours with stirring. The mixture was concentrated under reduced pressure, and the mixture was then partitioned between CHCl₃ and 10% aqueous K₂CO₃ solution. The CHCl₃ phase was separated, dried over MgSO₄ and concentrated. The residue was chromatographed over a column of silica gel, and the fractions eluted with CHCl₃-methanol (v/v, 9:1) were concentrated and recrystallized from diethyl ether/n-hexane to give 3-(2-chlorophenyl)-6-ethoxycarbonyl-5,7-dimethyl-1-[3-(N-benzyl-N-methylamino)propyl]-2,4(1H, 3H)-quinazolinedione (355 mg, 66.5%) melting at 145°–146° C. After treating the crystals with ethanol containing hydrogen chloride and recrystallizing from ethanol/diethyl ether, the hydrochloride melting at 207°–209° C. was obtained.

EXAMPLE 25

A mixture consisting of a portion (229 mg) of the product of Example 22 and unsym-diethylethylenediamine (1 ml) was heated at 80°-85° C. for 5 hours. After cooling, the mixture was diluted with diethyl ether and allowed to stand in a refrigerator overnight. The resulting precipitate was filtered off and recrystallized from ethyl acetate/diethyl ether to give 3-(2-chlorophenyl)-1-[2-(N,N-diethylamino)ethyl]carbamoylmethyl-6-ethoxycarbonyl-5,7-dimethyl-2,4-(1H, 3H)-quinazolinedione (164 mg, 62%) melting at 193°-194° C.

EXAMPLE 26

A mixture consisting of a portion (100 mg) of the product of Example 22 and conc. hydrochloric acid (5 ml) was stirred at 50° C. for 15 hours. The resulting precipitate was filtered off, washed with ether, and air dried. The crystalline mass was recrystallized from diethyl ether to give 1-carboxy-3-(2-chlorophenyl)-6-ethoxycarbonyl-5,7-dimethyl-2,4(1H,3H)-quinazolinedione (72 mg) melting at 182°-183° C.

EXAMPLE 27

A mixture of a portion (100 mg) of the product of Example 22 and thionyl chloride (1 ml) was refluxed for 30 minutes. The excess thionyl chloride was evaporated off, and the residue was treated with concentrated aqueous ammonia (10 ml). After stirring at room temperature for 3 hours, the precipitate was filtered off, washed with water, and recrystallized from methanol to give 1-carbamoylmethyl-3-(2-chlorophenyl)-6-ethoxycarbonyl-5,7-dimethyl-2,4(1H,3H)-quinazolinedione (70 mg, 70%) melting at 285°-287° C. MS: m/e, 429, 394. NMR: δ (ppm, DMSO-$d_6$) 1.32 (3H), 2.34 (3H, s), 2.59 (3H, s), 4.36 (2H, q), 4.77 (2H, s), 7.10 (1H, s), 7.51 (4H, m).

EXAMPLE 28

A mixture consisting of a portion (215 mg) of the product of Example 26 and thionyl chloride (2 ml) was refluxed for 30 minutes. The excess thionyl chloride was evaporated off, and the residue was dissolved in dry benzene (6 ml). After addition of N-methylpiperazine (650 mg), the mixture was stirred at room temperature for 3 hours. The mixture was partitioned between benzene and water. The benzene layer was separated, and the water phase was extracted with $CH_2Cl_2$. The benzene solution and $CH_2Cl_2$ extracts were combined, dried over $MgSO_4$ and concentrated. The residue was chromatographed over silica gel, and the fractions eluted with $CHCl_3$-methanol (v/v, 50:1) were concentrated and recrystallized from ethyl acetate/diethyl ether to give 3-(2-chlorophenyl)-6-ethoxycarbonyl-5,7-dimethyl-(4-methyl-1-piperazinyl)carbonylmethyl-2,4(1H,3H)-quinazolinedione (183 mg, 71.5%) melting at 64°-65° C.

EXAMPLE 29

A portion (0.053 g) of 50% sodium hydride suspension in mineral oil was added to a solution of 6-ethoxycarbonyl-5,7-dimethyl-3-[2-(trifluoromethyl)phenyl]-2,4-(1H,3H)-quinazolinedione (0.4 g) in dried dimethylformamide (10 ml). After the mixture was stirred at 150° C. for 20 minutes, 4-cinnamoyl-1-(2-chloroethyl)piperazine (0.274 mg) was added and the mixture was heated at 150° C. for 4 hours with stirring. The solvent was evaporated off, and the residue was extracted with $CHCl_3$. The $CHCl_3$ extract was washed with 10% aqueous $K_2CO_3$ solution, dried over $Na_2SO_4$ and concentrated. The residue was chromatographed over silica gel, and the fractions eluted with $CHCl_3$-methanol (v/v, 9:1) were concentrated. The concentrates were recrystallized from diethyl ether-n-hexane to give 1-[2-(4-cinnamoyl-1-piperazinyl)ethyl]-6-ethoxycarbonyl-5,7-dimethyl-3-[2-(trifluoromethyl)phenyl]-2,4(1H,3H)-quinazolinedione melting at 119°-120° C. (0.482 g, 75.5%).

EXAMPLE 30

1-(2-Chloroethyl)piperidine hydrochloride (0.85 g) and sodium hydrogen carbonate (1.5 g) were added to a solution of 6-amino-3-ethoxycarbonyl-2,4-dimethylbenzoic acid (1.0 g) in ethanol (10 ml) and water (10 ml). The mixture was stirred at room temperature for 24 hours and then its pH was adjusted to 4-5 by addition of 10% hydrochloric acid. The solution was concentrated under reduced pressure, and the resulting residue was extracted with $CHCl_3$. The $CHCl_3$ extracts were combined, washed with water, and dried over anhydrous $MgSO_4$. The solvent was evaporated, and the residue was recrystallized from ethanol/diethyl ether to give 3-ethoxycarbonyl-2,4-dimethyl-6-(2-piperidinoethylamino)benzoic acid dihydrochloride (1.2 g, 68%). MS: m/e, 348(M+), 304, 303, 259. NMR: δ (ppm $CDCl_3$), 1.37 (3H, t), 1.75 (6H, b), 2.25 (3H, s), 2.41 (3H, s), 3.00 (6H, b), 3.65 (2H, b), 4.36 (2H, q), 6.33 (1H, s), 8.20 (2H, b).

Triethylamine (0.58 g) and o-(trifluoromethyl)phenyl isocyanate (0.53 g) were added to a solution of the benzoic acid described above (1.2 g) in diethyl ether (20 ml), and the mixture was refluxed for 4 hours. After evaporating the solvent, the residue was dissolved in ethanol (20 ml) containing 10% hydrogen chloride. The solution was refluxed for one hour and then concentrated. The concentrate was diluted with water and extracted with $CHCl_3$, and the $CHCl_3$ extracts were combined, washed successively with 10% aqueous $Na_2CO_3$ solution and brine, and dried over anhydrous $Na_2SO_4$. The solvent was evaporated, and the residue was recrystallized from diethyl ether-n-hexane to give 6-ethoxycarbonyl-5,7-dimethyl-1-(2-piperidinoethyl)-3-[2-(trifluoromethyl)phenyl]-2,4(1H,3H)-quinazolinedione (1.1 g, 72%) melting at 144°-145° C. MS: m/e, 517(M+), 498, 472, 433, 406. NMR: δ (ppm. $CDCl_3$), 1.40 (3H, t), 1.50 (6H, b), 2.45 (3H, s), 2.52 (6H, t), 2.70 (3H, s), 4.30 (2H, t), 4.45 (2H, q), 7.10-7.80 (5H, m).

EXAMPLES 31-121

In a similar manner to Examples 21-25 or 27-30, the following compounds of formula ($I_b$) were obtained in 50-80% yields as shown in Table II.

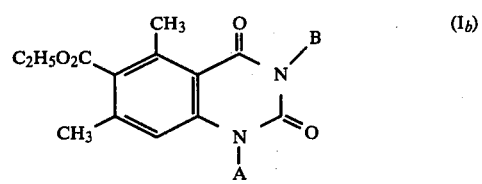

TABLE II

| No. | Compound of formula (I_b) A | B | Melting point (°C.) | Recrystallization solvent |
|---|---|---|---|---|
| 31 | methyl | o-Chlorophenyl | 216–217 | ethanol |
| 32 | 2-(N,N—dimethylamino)ethyl | " | 192–913 (hydrochloride:232–235) | ethanol/ether (") |
| 33 | 2-piperidinoethyl | " | 138–139 (hydrochloride:243–244) | ethano/ether (") |
| 34 | 2-morpholinoethyl | " | hydrochloride:165–166 | ethanol/ether |
| 35 | t-butoxycarbonylmethyl | " | 184–185 | ether |
| 36 | 3-(ethoxycarbonyl)propyl | " | 82–83 | ether |
| 37 | 2-(1-pyrrolidinyl)ethyl | " | 144–145 | ether/n-hexane |
| 38 | 2-piperidinoethyl | m-Chlorophenyl | 153–154 (hydrochloride:230–232) | ethanol (") |
| 39 | 3-piperidinopropyl | " | 151–152 (hydrochloride:236–238) | ethanol (ethanol/ether) |
| 40 | ethoxycarbonylmethyl | " | 157–158 | methanol |
| 41 | 2-piperidinoethyl | p-Chlorophenyl | 182–183 (hydrochloride:241–244) | ethanol (") |
| 42 | 3-piperidinopropyl | " | 158–159 (hydrochloride:200–202) | methanol (ethanol/ether) |
| 43 | ethoxycarbonylmethyl | " | 159–160 | methanol (ethanol/ether) |
| 44 | 3-(N,N—dimethylamino)propyl | o-fluorophenyl | 144–145 (hydrochloride:240–241) | ethanol/ether (") |
| 45 | 3-(N,N—dimethylamino)propyl | o-tolyl | 149–150 (hydrochloride:222–223) | ethanol/ether (") |
| 46 | 2-piperidinoethyl | m-tolyl | 126–127 (hydrochloride:235–236) | methanol (methanol/ether) |
| 47 | 3-piperidinopropyl | " | hydrochloride:222–225 | acetone |
| 48 | 2-piperidinoethyl | m-nitrophenyl | 163–165 (hydrochloride:255–258) | methanol (methanol/ether) |
| 49 | 3-piperidinopropyl | " | 135–136 | methanol (methanol/ether) |
| 50 | —CH₂CH₂—N(CH₃)-pyrrolidinyl | " | 207–210 | methanol |
| 51 | —CH₂CH₂—N(CH₃)-pyrrolidinyl | o-CF₃—phenyl | hydrochloride:212–213 | ethanol-ether |
| 52 | —CH₂CH₂—N(CH₃)-pyrrolidinyl | o-Chlorophenyl | 160–162 (hydrochloride:210–211) | methanol (acetone/ether) |
| 53 | 2-piperidinoethyl | o-nitrophenyl | hydrochloride:206.5–208 | ethanol |
| 54 | 2-piperidinoethyl | o-CF₃—phenyl | hydrochloride:216–218 | ethanol/ether |
| 55 | 2-(N,N—dimethylamino)ethyl | " | hydrochloride:229–232 | " |
| 56 | 3-(N,N—diethylamino)propyl | o-CF₃—phenyl | hydrochloride:201–203 | ethanol/ether |
| 57 | 2-piperidinoethyl | m-CF₃—phenyl | hydrochloride:225–228 | " |
| 58 | 2-piperidinoethyl | p-tolyl | 147–148 (hydrochloride:231–234) | methanol (") |
| 59 | 2-piperidinoethyl | m-methoxyphenyl | 107–108 (hydrochloride:242–244) | methanol (methanol/ether) |
| 60 | 3-piperidinopropyl | " | 137–139.5 (hydrochloride:171–174) | methanol (methanol/ether) |
| 61 | 3-piperidinopropyl | p-methoxyphenyl | 129–130 (hydrochloride:223–225) | acetone |
| 62 | 3-(N,N—dimethylamino)propyl | o-nitrophenyl | 150–152 | ether |
| 63 | 2-piperidinoethyl | phenyl | hydrochloride:216–218 | CHCl₃/ether |
| 64 | ethoxycarbonylmethyl | o-nitrophenyl | 150–152 | ether |
| 65 | 3-(N,N—dimethylamino)propyl | o-CF₃—phenyl | 150–151 | ether |
| 66 | 2-(N,N—diethylamino)ethyl | " | hydrochloride:178.5–180 | ethanol/ether |
| 67 | 3-piperidinopropyl | " | hydrochloride:208–210 | ethanol/ether |
| 68 | 2-morpholinoethyl | " | hydrochloride:146–149 | ethanol/ether |
| 69 | ethoxycarbonylmethyl | " | 176–178 | ethanol |
| 70 | 2-(N,N—diisopropyl)ethyl | " | hydrochloride:219–221 | ethanol/ether |
| 71 | —CH₂CH₂N⌒(CH₂)₆ | " | hydrochloride:200–201 | ethanol/ether |

TABLE II-continued

| No. | Compound of formula (I$_b$) A | B | Melting point (°C.) | Recrystallization solvent |
|---|---|---|---|---|
| 72 | 2-(N,N—dimethylamino)-1-methylethyl | o-CF$_3$—phenyl | hydrochloride:229–230 | ethanol/ether |
| 73 | 3-(N,N—dimethylamino)-2-methylpropyl | " | hydrochloride:203–205 | ethanol/ether |
| 74 | CH$_2$CH$_2$N⟨⟩(CH$_2$)$_7$ | " | hydrochloride:213–216 | ethanol/ether |
| 75 | CH$_2$CH$_2$N—⟨piperidinyl⟩—CH$_3$ | o-CF$_3$—phenyl | hydrochloride:238–243 | ethanol/ether |
| 76 | (CH$_2$)$_2$N—⟨piperidinyl⟩—(CH$_2$)$_3$—phenyl | " | 184–185 | CHCl$_3$/n-hexane |
| 77 | 2-piperidinoethyl | p-nitrophenyl | 187–188 | methanol |
| 78 | 2-piperidinoethyl | 2-bromo-4-methylphenyl | hydrochloride:221–223 | CHCl$_3$/ether |
| 79 | 3-(N,N—diethylamino)propyl | 4-(diethylamino)-2-methylphenyl | di-hydrochloride:155–157 | ethanol/ether |
| 80 | 2-(N—benzyl-N—methylamino)-ethyl | o-CF$_3$—phenyl | hydrochloride:179.5–182 | ethanol/ether |
| 81 | 3-(N—benzyl-N—methylamino)-propyl | o-Chlorophenyl | 145–146 (hydrochloride:207–209) | ether/n-hexane (ethanol/ether) |
| 82 | 3-(N—benzyl-N—methylamino)-propyl | m-nitrophenyl | 117–118 (hydrochloride:220–224) | methanol (acetone/ether) |
| 83 | 3-(N—benzyl-N—methylamnio)-propyl | o-CF$_3$—phenyl | hydrochloride:207–209 | ethanol/ether |
| 84 | 3-(N—benzyl-N—methylamino)-propyl | 2,4-dichlorophenyl | hydrochloride:203–205 | ethanol/ether |
| 85 | 2-piperidinoethoxycarbonyl-methyl | o-Chlorophenyl | hydrochloride:183–185 | ethanol/ether |
| 86 | 2-piperidinoethoxycarbonyl-methyl | p-Chlorophenyl | hydrochloride:210–212 | ethanol/ether |
| 87 | 2-piperidinoethoxycarbonyl-methyl | o-CF$_3$—phenyl | hydrochloride:197–200 | ethanol/ether |
| 88 | 3-(N,N—dimethylamino)-propoxycarbonylmethyl | o-Chlorophenyl | hydrochloride:178–180 | ethanol/ether |
| 89 | 2-(N,N—dimethylamino)-ethoxycarbonylmethyl | o-Chlorophenyl | hydrochloride:192–194 | ethanol/ether |
| 90 | 2-(N,N—dimethylamino)-ethoxycarbonylmethyl | o-CF$_3$—phenyl | hydrochloride:179–181 | ethanol/ether |
| 91 | 3-(N—benzyl-N—methylamino)-propoxycarbonylmethyl | o-Chlorophenyl | 111–112 (hydrochloride:205–207) | ether (ethanol) |
| 92 | 2-(N—benzyl-N—methylamino)-ethoxycarbonylmethyl | o-nitrophenyl | hydrochloride:125–127 | ethanol/ether |
| 93 | 2-(2-morpholinoethylamino)-ethoxycarbonylmethyl | o-nitrophenyl | hydrochloride:159–162 | ethanol/ether |
| 94 | CH$_2$—⟨piperidinyl-N—CH$_3$⟩ | m-nitrophenyl | 129–132 | diethyl ether |
| 95 | CH$_2$—⟨piperidinyl-N—CH$_3$⟩ | o-CF$_3$—phenyl | hydrochloride:200–202 | ethanol/ether |
| 96 | CH$_2$—⟨piperidinyl-N—CH$_3$⟩ | o-Chlorophenyl | 142–145 (hydrochloride:206–208) | methanol (ethanol) |

TABLE II-continued

| No. | Compound of formula (I_b) A | B | Melting point (°C.) | Recrystallization solvent |
|---|---|---|---|---|
| 97 | CH₂CH₂—N(2-methylpiperidinyl, with CH₃ groups) (labeled 100) | o-Chlorophenyl | 134–135 (hydrochloride:221–224) | methanol (acetonediethyl ether) |
| 98 | (CH₂)₃CONH₂ | o-Chlorophenyl | 175–176 | ethyl acetate/ether |
| 99 | (N—benzyl-N—methyl)-carbamoylmethyl | o-Chlorophenyl | 172–173 | ethyl acetate/ether |
| 100 | 2-hydroxyethyl | o-CF₃—phenyl | 106–108 | ether/cyclohexane |
| 101 | CH₂CONHCH₃ | o-Chlorophenyl | 249–250 | methanol |
| 102 | CH₂CON(piperazinyl)N—CH₃ | o-Chlorophenyl | 64–65 | ethyl acetate-ether |
| 103 | CH₂CONHCH₂CH₂N(piperidinyl) | o-Chlorophenyl | 179–180 | ethyl acetate |
| 104 | CH₂CONHCH₂CH₂N(piperidinyl) | p-Chlorophenyl | 247–248 (hydrochloride:187–188) | methanol (methanol-ether) |
| 105 | CH₂CONHCH₂CH₂N(piperidinyl) | m-Chlorophenyl | 211–212 (hydrochloride:205–209) | methanol (ethanol/ether) |
| 106 | CH₂CONHCH₂CH₂N(piperidinyl) | m-nitrophenyl | 135–136 | ethyl acetate/ether |
| 107 | CH₂CONHCH₂CH₂N(piperidinyl) | o-CF₃—phenyl | 177–179 | ethyl acetate/ether |
| 108 | CH₂CONH(CH₂)₃N(morpholinyl)O | o-Chlorophenyl | 197–198 | ethyl acetate/ether |
| 109 | CH₂CONH(CH₂)₃N(C₂H₅)₂ | o-Chlorophenyl | 173–175 | ethyl acetate/ether |
| 110 | CH₂CONH(CH₂)₂N(C₂H₅)₂ | o-Chlorophenyl | 193–194 | ethyl acetate/ether |
| 111 | CH₂CON(piperidinyl) | o-Chlorophenyl | 173–175 | ethyl acetate/ether |
| 112 | CH₂CH₂—N(piperazinyl with CH₂C₆H₅) | o-Chlorophenyl | 157–158 | ether/n-hexane |

TABLE II-continued

| No. | Compound of formula (I_b) A | B | Melting point (°C.) | Recrystallization solvent |
|---|---|---|---|---|
| 113 | CH$_2$CH$_2$—N(piperazine)-N-C$_6$H$_5$ | o-Chlorophenyl | 83–95 | methanol |
| 114 | CH$_2$CONH(CH$_2$)$_2$N(piperazine)N—CN(CH$_3$)$_2$ (with C=O) | o-CF$_3$—phenyl | 104–105 | CHCl$_3$/n-hexane |
| 115 | benzyl | o-Chlorophenyl | 160–161 | ether/n-hexane |
| 116 | 3',4'-dimethoxybenzyl | o-Chlorophenyl | 167–168 | ethanol/n-hexane |
| 117 | 2-pyridylmethyl | o-Chlorophenyl | 161–162 | ethanol |
| 118 | 3-pyridylmethyl | o-Chlorophenyl | 192–193 | ether |
| 119 | 4-pyridylmethyl | o-Chlorophenyl | 128–130 | ethanol |
| 120 | 4-pyridylmethyl | o-CF$_3$—phenyl | hydrochloride:189–191 | ethanol |
| 121 | 4-pyridylmethyl | o-nitrophenyl | hydrochloride:220–222 | ethanol |

EXAMPLES 122–137

In a similar manner to Examples 21–25 or 27–29, the following compound of formula (I$_c$) shown in Table III were obtained in 40–60% yields, according to the reaction scheme shown below.

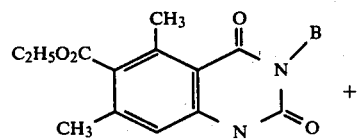

+

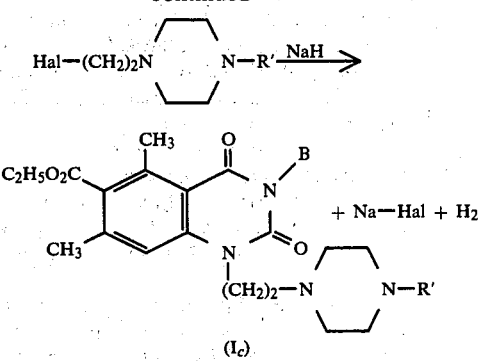

+ Na—Hal + H$_2$ (I$_c$)

wherein Hal represents a halogen atom.

TABLE III

| No. | Compound of formula (I$_c$) R' | B | Melting point (°C.) | Recryst Solvent |
|---|---|---|---|---|
| 122 | phenyl | o-Chlorophenyl | 128–129 (hydrochloride: 225–227) | methanol (methanol/ether) |
| 123 | phenyl | o-CF$_3$—phenyl | hydrochloride: 192–194 | CHCl$_3$/ether |
| 124 | 2-Chlorophenyl | m-nitrophenyl | 134–140 (dihydrochloride: 159–165) | acetone/ether (methanol/ether) |
| 125 | 2-Chlorophenyl | o-Chlorophenyl | 100–101 (dihydrochloride: 211–216) | ether(ethanol) |
| 126 | benzyl | o-Chlorophenyl | 165–166 (dihydrochloride: 226–229) | ether/n-hexane (ethanol) |
| 127 | benzyl | o-CF$_3$—phenyl | dihydrochloride: 208–210 | ethanol/ether |
| 128 | phenethyl | o-CF$_3$—phenyl | dihydrochloride: 215–218 | ethanol |
| 129 | 3-phenylpropyl | o-CF$_3$—phenyl | dihydrochloride: 181.5–183 | ethanol/ether |
| 130 | 3-phenylpropyl | o-Chlorophenyl | dihydrochloride: 240–242 | ethanol/n-hexane |
| 131 | CH$_2$CH=CHC$_6$H$_5$ | o-nitrophenyl | dihydrochloride: 162–164 | ethanol |
| 132 | CH$_2$—C(CH$_3$)=CHC$_6$H$_5$ | o-CF$_3$—phenyl | dihydrochloride: 186–188 | ethanol |
| 133 | 2',3',4'-dimethoxybenzyl | o-CF$_3$—phenyl | dihydrochloride: 160–163 | ethanol/ether |
| 134 | 3',4'-dimethoxyphenetyl | o-CF$_3$—phenyl | dihydrochloride: 172–174 | ethanol/ether |
| 135 | 2-(α-thenyl)ethyl | o-CF$_3$—phenyl | dihydrochloride: 173–174 | ethanol/ether |

TABLE III-continued

| No. | R' | B | Melting point (°C.) | Recryst Solvent |
|---|---|---|---|---|
| | Compound of formula (I_c) | | | |
| 136 | CH₂CO–N(2,6-dimethylpiperidino) [CH₂CON with piperidine ring bearing two CH₃ groups] | o-Chlorophenyl | dihydrochloride: 220–222 | ethanol/ether |
| 137 | N—(2,6-dimethylphenyl)carbamoylmethyl | o-Chlorophenyl | dihydrochloride: 180–182 | ethanol/ether |

EXAMPLE 138

A portion (0.376 g) of 50% sodium hydride suspension was added to a solution of 6-ethoxycarbonyl-5,7-dimethyl-3-[2-(trifluoromethyl)phenyl]-2,4(1H,3H)-quinazolinedione. (3.0 g) in dimethylformamide (75 ml), and the mixture was stirred at 150° C. for 20 minutes. After dropwise addition of a solution of 4-benzyloxycarbonyl-1-(2-chloroethyl)piperazine (2.21 g) in dimethylformamide (15 ml), the reaction mixture was further stirred for 5.5 hours at 150° C. The solvent was then evaporated off, and the residue was partitioned between CHCl₃ and 10% aqueous K₂CO₃ solution. The CHCl₃ phase was separated, dried over anhydrous K₂CO₃ and concentrated. The residue was recrystallized from diethyl ether/n-hexane to give 1-[2-(4-benzyloxycarbonyl-1-piperadinyl)ethyl]-6-ethoxycarbonyl-5,7-dimethyl-3-[2-(trifluoromethyl)phenyl]-2,4(1H,3H)-quinazolinedione (3.50 g, 72.6%) melting at 139°–140° C.

A portion (2.00 g) of the above product was dissolved in ethyl acetate (8 ml), and after addition of acetic acid (5.9 ml) containing 25% hydrogenbromide, the mixture was stirred at room temperature for 2 hours and then diluted with diethyl ether. The resulting precipitate was filtered off and washed with diethyl ether to give crude 6-ethoxycarbonyl-5,7-dimethyl-1-[2-(1-piperazinyl)ethyl]-3-[2-(trifluoromethyl)phenyl]2,4(1H,3H)-quinazolinedione hydrobromide (1.94 g, 93%).

A portion (0.200 g) of the above hydrobromide was added to a mixture of ethyl acetate (10 ml), water (2 ml) and sodium hydrogencarbonate (99 mg). To the mixture was added a solution of 2-thenoyl chloride (55 mg) in ethyl acetate (1 ml), and the mixture was stirred for 2 hours at room temperature. The organic layer and ethyl acetate extracts were combined, dried over anhydrous Na₂SO₄ and concentrated. The residue was recrystallized from diethyl ether/n-hexane to give 6-ethoxycarbonyl-5,7-dimethyl-1-{2-[4-(2-thenoyl)-1-pieradinyl]ethyl}-3-[2-(trifluoromethyl)phenyl]-2,4-(1H,3H)-quinazolinedione (0.135 g, 73.1%) melting at 148°–149° C. MS, m/e, 628(M⁺), 583, 501, 476, 433, 406. NMR: δ (ppm, CDCl₃), 1.41 (3H, t), 2.46 (3H, s), 2.5–2.9 (6H, m), 2.72 (3H, s), 3.6–3.9 (4H, m), 4.2–4.6 (2H, m), 4.46 (2H, q), 6.9–8.0(8H, m).

EXAMPLES 139–142

In a similar manner to Example 138, the following products were prepared by reacting 6-ethoxycarbonyl-5,7-dimethyl-1-[2-(1-piperazinyl)ethyl]-3-[2-(trifluoromethyl)phenyl-2,4(1H,3H)-quinazolinedione with 2-furoyl chloride (Example 139), isonicotinoyl chloride (Example 140), phenylacetyl chloride (Example 141), and phenyl isocyanate (Example 142), respectively.

EXAMPLE 139

6-ethoxycarbonyl-5,7-dimethyl-1-{2-[4-(2-furoyl)-1-piperazinyl]-ethyl}-3-[2-(trifluoromethyl)phenyl]-2,4(1H,3H)-quinazolinedione, hydrochloride, mp. 183°–185° C., recryst. from ethanol/ether.

EXAMPLE 140

6-ethoxycarbonyl-5,7-dimethyl-1-{2-[4-isonicotinoyl-1-piperazinyl]ethyl}-3-[2-(trifluoromethyl)phenyl]-2,4(1H,3H)-quinazolinedione, mp. 166°–167° C. recryst. from ethanol/water.

EXAMPLE 141

6-ethoxycarbonyl-5,7-dimethyl-1-{2-[4-phenylacetyl-1-piperazinyl]ethyl}-3-[2-trifluoromethyl)phenyl]-2,4(1H,3H)-quinazolinedione, mp. 121°–122° C., recryst. from ether/n-hexane.

EXAMPLE 142

6-ethoxycarbonyl-5,7-dimethyl-1-{2-[4-(N-phenylcarbamoyl)-1-piperazinyl]ethyl}-3-[2-(trifluoromethyl)phenyl]-2,4(1H,3H)-quinazolinedione, mp. 200°–201° C., recryst. from ethanol/ether.

EXAMPLE 143

In a similar manner to Example 139, 6-ethoxycarbonyl-5,7-dimethyl-1-{2-[4-(2-nitrobenzoyl)]-1-piperazinyl}-3-(2-nitrophenyl)-2,4(1H,3H)-quinazolinedione melting 188°–189° C. (recryst. from ethanol) was obtained.

EXAMPLE 144

A mixture of 3-(2-chlorophenyl)-1-ethoxycarbonylmethyl-6-ethoxycarbonyl-5,7-dimethyl-2,4(1H,3H)-quinazolinedione (459 mg) and N-(2-ethylamino)piperazine (2 g) was heated at 80° C. for 5 hours with stirring. After cooling, the mixture was diluted with diethyl ether (20 ml) and stirred at room temperature overnight, The resulting crystalline precipitate was filtered off, washed throughly with diethyl ether, and recrystallized from methanol/diethyl ether to give 3-(2-chlorophenyl)-6-ethoxycarbonyl-5,7-dimethyl-1-{N-[2-(1-piperazinyl)ethyl]carbamoylmethyl}-2,4(1H,3H)-quinazolinedione (370 mg, 68.3%) melting at 188°–190° C. MS, m/e: 541 (M⁺). NMR: δ (ppm, DMSO-d₆), 1.32 (3H, t), 2.33 (3H, s), 2.59 (3H, s), 2.15–2.9 (10H, m), 3.23 (2H, bt), 4.35 (2H, q), 4.79 (2H, s), 7.08 (1H, s), 7.3–7.8 (4H, m), 8.1 (1H, bs).

EXAMPLE 145

3-(4-chlorophenyl)-1-ethoxycarbonylmethyl-6-ethoxycarbonyl-5,7-dimethyl-2,4(1H,3H)-quinazolinedione was reacted with N-(2-ethylamino)piperazine in a similar manner to Example 144. 3-(4-Chlorophenyl)-6-ethoxycarbonyl-5,7-dimethyl-1-{N-[2-(1-piperazinyl)ethyl]carbamoylmethyl}-2,4(1H,3H)-quinazolinedione melting at 204°–206° C. (recryst. from ethanol) was obtained in 60.2% yield.

EXAMPLE 146

A portion (120 mg) of the product of Example 144 was dissolved in pyridine (1 ml). After addition of methyl isocyanate (70 mg), the mixture was stirred overnight. The solvent was evaporated off, and the residue was recrystallized from methanol/diethyl ether to give 3-(2-chlorophenyl)-6-ethoxycarbonyl-5,7-dimethyl-1-{N-[2-(4-N-methylcarbamoyl-1-piperazinyl)ethyl]carbamoylmethyl}-2,4(1H,3H)-quinazolinedione (86 mg, 70%) melting at 190°–191° C.

EXAMPLE 147

A portion of the product of Example 144 was reacted with phenyl isocyanate in a similar manner to Example 146 to give 3-(2-chlorophenyl)-6-ethoxycarbonyl-5,7-dimethyl-1-{N-[2-(4-N-phenylcarbamoyl-1-piperazinyl)ethyl]carbamoylmethyl}-2,4(1H,3H)-quinazolinedione melting at 145°–148° C. (recryst. from methanol/diethyl ether).

EXAMPLE 148

A portion of the product of Example 145 was reacted with phenyl isocyanate in a similar manner to Example 146 to give 3-(4-chlorophenyl)-6-ethoxycarbonyl-5,7-dimethyl-1-{N-[2-(4-phenylcarbamoyl-1-piperazinyl)ethyl]carbamoylmethyl}-2,4(1H,3H)-quinazolinedione melting at 246°–248° C. (recryst. from ethanol).

EXAMPLE 149

A portion of the product of Example 144 was reacted with acetic anhydride in a similar manner to Example 146 to give 1-{N-[2-(4-acetyl-1-piperazinyl)ethyl]carbamoylmethyl}3-(2-chlorophenyl)-6-ethoxycarbonyl-5,7-dimethyl-2,4(1H,3H)-quinazolinedione melting at 190°–191° C. (recryst. from methanol/diethyl ether).

TEST FOR BLOOD VESSEL RELAXING EFFECT

Albino rabbits weighing 2.5 to 3 kg were sacrificed by exsanguination. The thoracic aorta, superior mesenteric artery, and basilar artery were quickly excised. The arteries were detached from fats and connective tissues and then, cut at an angle of approximately 45° to the longitudinal axis into strips. The width and length of the strips were 2.5 mm and 30 mm in the case of aorta, 2 mm and 25 mm in mesenteric artery, and 1 mm and 20 mm in basilar artery, respectively. Each experiment was carried out in a conventional tissue bath. The composition of the bathing solution was as follows (in millimolar concentrations): NaCl, 115.0; KCl, 4.7; $CaCl_2 \cdot 2H_2O$, 2.5; $MgCl_2 \cdot 6H_2O$, 1.2; $NaHCO_3$, 25; $KH_2PO_4$, 1.2; and glucose 10.0. The tissue bath solutions were maintained at 37° C., and bubbled with a mixture of 95% $O_2$ and 5% $CO_2$. The upper end of the strip was connected to the lever of a force-displacement transducer by a silk thread. Initial resting tensions of 1.5 g, 1 g, and 0.5 g were applied to the aorta, mesenteric and basilar artery, respectively.

Before the experiments commenced, preparations were equilibrated for 2 hours in the bathing solution. During the equilibration period, the solutions were replaced every 30 minutes with fresh media. After equilibration, the strip was constricted by addition of potassium chloride in a concentration of 20 mM in the case of aorta and 25 mM in mesenteric and basilar artery. After the constriction induced by potassium chloride reached a maximum, a solution of test compound in water was added to the bath in the concentration indicated in Table IV, and the resulting relaxation was recorded. When the test compound was insoluble in water, solution of the test compound in dimethylsulfoxide was used. The amount of the dimethylsulfoxide was minimized so that the final concentration of the dimethylsulfoxide did not exceed 0.3%. At the end of each series of experiments, papaverine was added to the bath in a concentration of $3 \times 10^{-4}$ M in the case of aorta and $1 \times 10^{-4}$ M in mesenteric and basilar artery, and relaxation induced by papaverine was taken as 100%. The relaxing effects of test compounds shown in Table IV were expressed as percentages against the maximum relaxation induced papaverine. Each compound was tested three times and the relaxation effect was a mean value obtained from the three experiments.

TABLE IV

| | Relaxing effect (%) | | |
|---|---|---|---|
| Blood Concentration | Thoracic aorta $3 \times 10^{-5}$M | Mesenteric artery $3 \times 10^{-6}$M | Basilar artery $3 \times 10^{-6}$M |
| Test compound | | | |
| Papaverine (control) | 52 ± 2.1 | 42 ± 5.0 | 21 ± 3.3 |
| 3-(2-Chlorophenyl)-6-ethoxycarbonyl-2,5,7-trimethyl-4(3H)—quinazolinone | 68 ± 7.5 | 41 ± 6.7 | 62 ± 9.6 |
| 3-[2-(Trifluoromethyl)-phenyl]-6-ethoxycarbonyl-2,5,7-trimethyl-4(3H)—quinazolinone | 61 ± 7.5 | 24 ± 8.2 | 80 ± 9.6 |
| The compound of the present invention | | | |
| Compound No. 1 | 64 ± 5.0 | NT | NT |
| Compound No. 2 | 64 ± 5.0 | NT | NT |
| Compound No. 21 | 88.4 ± 5.4 | 39.5 ± 10.6 | 54 ± 4.7 |
| Compound No. 24 | 88.3 ± 4.3 | NT | NT |
| Compound No. 25 | 71.1 ± 5.9 | NT | NT |
| Compound No. 30 | 87.9 ± 3.7 | 99.5 ± 11.3 | 89.6 ± 7.2 |
| Compound No. 33 | 88.6 ± 2.2 | 91.0 ± 5.7 | 94.7 ± 4.1 |
| Compound No. 48 | 98.2 ± 6.2 | 92.2 ± 6.3 | 95.3 ± 3.9 |
| Compound No. 51 | 90.3 ± 4.5 | 90.2 ± 8.5 | 97.2 ± 8.6 |
| Compound No. 85 | 95.0 ± 8.2 | 78.7 ± 5.6 | 88.3 ± 7.2 |
| Compound No. 103 | 87.3 ± 4.2 | 68 ± 9.7 | 82 ± 10.1 |
| Compound No. 139 | 79.3 ± 3.5 | NT | NT |
| Compound No. 112 | 87 ± 6.3 | NT | NT |

NT = not tested

All of the above compounds of the present invention were tested in the form of hydrochloride, except No. 1 and 2.

Test for acute toxicity

A suspension of a test compound in 0.5% CMC aqueous solution containing Tween 80 was orally administered to mice, and during the following 8 days the number of dead mice was counted. The results is shown below.

| Test Compound | Dose | number of dead mice / number of test mice |
|---|---|---|
| Compound of No. 21 | 1,000 mg/kg | 0/6 |
| Compound of No. 30 | 1,000 mg/kg | 0/6 |

What is claimed is:

1. A 5,6,7-substituted-2,4(1H,3H)-quinazolinedione compound of the formula (I),

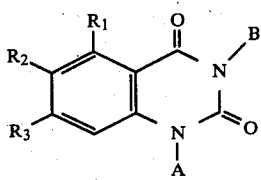

wherein
$R_1$ and $R_3$ independently represent (lower)alkyl;
$R_2$ represents (lower)alkoxycarbonyl;
B represents a (lower)alkyl, phenyl or phenyl substituted by one or two members selected from the group consisting of halogen atoms, (lower)alkyl, (lower)alkoxy, di(lower)alkylamino, methylenedioxy, trifluoromethyl, and nitro; and
A represents a member selected from the group consisting of (a) a hydrogen atom, (b) (lower)alkyl, (c) carboxy(lower)alkyl, (d) (lower)alkoxycarbonyl(-lower)alkyl, (e) hydroxy(lower)alkyl, (f) benzyl, (g) benzyl substituted by (1) nitro or (2) (lower)alkoxy, (h) pyridylmethyl, (i) disubstituted-amino (lower)alkyl substituted by (1) two (lower)alkyl, or (2) one (lower)alkyl and one of benzyl, tetramethylene, pentamethylene, pentamethylene substituted by (lower)alkyl, hexamethylene or heptamethylene, said methylene forming a heterocycle together with the nitrogen atom of the amino (lower)alkyl, (j) (lower)alkyl bearing a piperidine or pyrrolidine ring, the nitrogen atom of which is substituted by a (lower)alkyl, (k) a moiety of the formula

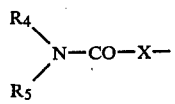

wherein X represents (lower)alkylene, $R_4$ represents a hydrogen atom or (lower)alkyl, $R_5$ represents a hydrogen atom, (lower)alkyl, di(lower)alkylamino-(lower)alkyl, benzyl, piperidino(lower)alkyl, morpholino(lower)alkyl, (1-piperazinyl)(lower)alkyl, (4-(lower)acyl-1-piperazinyl)(lower)alkyl, or (4-carbamoyl-1-piperazinyl)(lower)alkyl, the carbamoyl of which may be N-mono or disubstituted by (lower)alkyl or phenyl, and $R_4$ and $R_5$ can form together with the nitrogen atom a piperidine or 4-(lower)alkylpiperazine ring,
(l) moiety of the formula

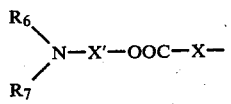

wherein X' and X represent independently (lower)alkylene, $R_6$ represents (lower)alkyl, $R_7$ represents (lower)alkyl, benzyl, piperidino(lower)alkyl, or morpholino(lower)alkyl, and $R_6$ and $R_7$ can form together with the nitrogen atom a piperidine ring,
(m) a moiety of the formula

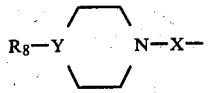

wherein X represents (lower)alkylene, Y represents a nitogen atom or methine, $R_8$ represents a hydrogen atom, (lower)alkyl, phenyl, phenyl(lower)alkyl, or phenyl(lower)alkene, the phenyl groups of which may be mono- or disubstituted by a chlorine atom, methoxy, benzoyl, benzoyl substituted by a halogen atom, nitro or methoxy, phenylacetyl, benzyloxycarbonyl, cinnamoyl, thenoyl, furoyl, or N-phenylcarbamoyl, provided that when Y is a methine $R_8$ is not hydrogen nor alkyl, and
(n) a moiety of the formula

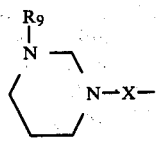

wherein X represents (lower)alkylene, and $R_9$ represents phenyl or benzyl;
or an acid addition salt thereof.

2. The compound of claim 1, which is 3-(2-chlorophenyl)-6-ethoxycarbonyl-5,7-dimethyl-2,4(1H,3H)-quinazolinedione.

3. The compound of claim 1, which is 6-ethoxycarbonyl-5,7-dimethyl-3-[2-(trifluoromethyl)phenyl]-2,4(1H,3H)-quinazolinedione.

4. The compound of claim 1, which is 3-(2-chlorophenyl)-6-ethoxycarbonyl-5,7-dimethyl-1-(2-piperidinoethyl)-2,4(1H,3H)-quinazolinedione.

5. The compound of claim 1, which is 6-ethoxycarbonyl-5,7-dimethyl-1-(2-piperidinoethyl)-3-[2-(trifluoromethyl)phenyl]-2,4(1H,3H)-quinazolinedione.

6. The compound of claim 1, which is 3-(2-chlorophenyl)-5,7-dimethyl-1-[2-(1-methylpyrrolidin-2-yl)ethyl]-2,4(1H,3H)-quinazolinedione.

7. The compound of claim 1, which is 6-ethoxycarbonyl-5,7-dimethyl-1-[2-(1-methylpyrrolidin-2-yl)ethyl]-3-[2-(trifluoromethyl)phenyl]-2,4(1H,3H)-quinazolinedione.

8. The compound of clam 1, which is 3-(2-chlorophenyl)-6-ethoxycarbonyl-5,7-dimethyl-1-[2-(2,6-dimethylpiperidin-1-yl)ethyl]-2,4(1H,3H)-quinazolinedione.

9. The compound of claim 1 in which $R_1$ and $R_3$ independently represent $C_1$-$C_3$ alkyl, and $R_2$ represents methoxy, ethoxy, propoxy, isopropoxy, n-butoxy, or isobutoxy.

10. The compound of claim 1 or claim 9 wherein B represents a $C_1$-$C_3$ alkyl, phenyl, or phenyl substituted by one or two members selected from the group consisting of chlorine, bromine, fluorine, $C_1$-$C_3$ alkyl, $C_1$-$C_4$ alkoxy, di-($C_1$-$C_3$ alkyl), amino, methylenedioxy, trifluoromethyl, and nitro.

11. The compound of claim 1 or claim 9 wherein A represents a member selected from the group consisting of
(a) hydrogen,
(b) ($C_1$-$C_4$)alkyl,
(c) carboxy($C_1$-$C_4$)alkyl,
(d) ($C_1$-$C_4$)alkoxycarbonyl($C_1$-$C_4$)alkyl,
(e) hydroxy($C_1$-$C_4$)alkyl,
(f) benzyl,
(g) benzyl substituted by (1) nitro or (2) ($C_1$-$C_4$) alkoxy,
(h) pyridyl methyl,
(i) di($C_1$-$C_4$)alkyl substituted amino ($C_1$-$C_4$) alkyl,
(i)' amino ($C_1$-$C_4$)alkyl disubstituted by a ($C_1$-$C_4$) alkyl and one of benzyl, tetramethylene, pentamethylene, pentamethylene mono- or di-substituted by ($C_1$-$C_3$)alkyl, hexamethylene or heptamethylene, said methylene groups forming a heterocyclic together with the nitrogen atom of the amino ($C_1$-$C_4$)alkyl,
(j) ($C_1$-$C_4$) alkyl bearing a piperidine or pyrrolidine ring, the nitrogen atom of which is substituted by a ($C_1$-$C_4$) alkyl,
(k) a moiety of formula

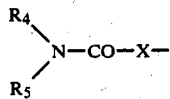

wherein X represents methylene, ethylene, propylene, tetramethylene or 2-methylpropylene, $R_4$ represents hydrogen or ($C_1$-$C_4$)alkyl, $R_5$ represents hydrogen, ($C_1$-$C_3$)alkyl, di-($C_1$-$C_3$)alkyl substituted amino ($C_1$-$C_3$)alkyl, benzyl, piperidino-($C_1$-$C_4$)alkyl, morpholino-($C_1$-$C_4$)alkyl, (1-piperazinyl)-($C_1$-$C_4$)alkyl, or (4-($C_1$-$C_4$)acyl-1-piperazinyl)-($C_1$-$C_4$)alkyl or $R_4$, $R_5$ and the nitrogen atom can form a piperidine of 4-($C_1$-$C_3$)alkyl-piperizine ring,
(l) a moiety of formula

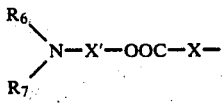

wherein X' and X represent independently from each other, ($C_1$-$C_4$)alkylene, $R_6$ represents ($C_1$-$C_3$)alkyl, and $R_7$ represents ($C_1$-$C_4$)alkyl, or morpholino ($C_1$-$C_4$)alkyl, or $R_6$, $R_7$ together with the nitrogen atom can form a piperidine ring,
(m) a moiety of formula

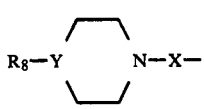

wherein X represents ($C_1$-$C_4$)alkylene, Y represents nitrogen or methine and $R_8$ represents hydrogen, ($C_1$-$C_4$)alkyl, phenyl, phenyl($C_1$-$C_4$)alkyl, phenyl ($C_1$-$C_4$)alkene wherein the phenyl groups may be mono- or di-substituted by a chlorine atom or a methoxy group, benzoyl, benzoyl substituted by halogen or methoxy, phenylacetyl, benzyloxycarbonyl, cinnamoyl, thenoyl, furoyl or N-phenylcarbomoyl, provided that when Y is methine, $R_8$ is neither hydrogen nor alkyl and
(n) a moiety of the formula

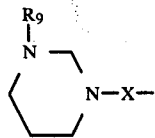

wherein X represents ($C_1$-$C_4$)alkylene and $R_9$ represents phenyl or benzyl,
or an acid addition salt thereof.

12. A 5,6,7-substituted-2,4(1H,3H)quinazolinedione compound of the formula

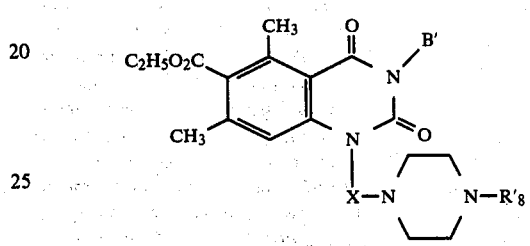

wherein
B' represents phenyl substituted by up to two members selected from the group consisting of halogen atoms, $C_1$-$C_3$alkyl, trifluoromethyl and nitro,
X represents $C_1$-$C_4$alkylene, and
$R_8'$ represents phenyl or phenyl($C_1$-$C_4$)alkyl.

13. A vasodilating and hypotensive composition composed of an effective amount of a compound selected from 5,6,7-substituted-2,4(1H,3H)-quinazolinedione compounds and their pharmaceutically acceptable acid addition salts, and a pharmaceutically acceptable diluent or carrier, said quinazolinedione compound being of the following formula

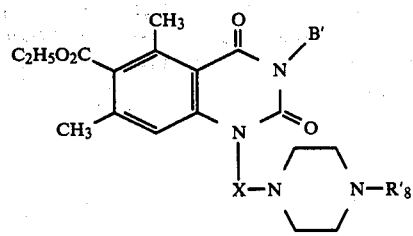

wherein
B' represents phenyl substituted by up to two members selected from the group consisting of halogen atoms, $C_1$-$C_3$alkyl, trifluoromethyl and nitro,
X represents $C_1$-$C_4$alkylene, and
$R_8'$ represents phenyl or phenyl($C_1$-$C_4$)alkyl.

14. A vasodilating and hypotensive composition composed of an effective amount of a compound selected from 5,6,7-substituted-2,4(1H,3H)-quinazolinedione compounds and their pharmaceutically acceptable acid addition salts, and a pharmaceutically acceptable diluent or carrier, said quinazolinedione compound being of the following formula

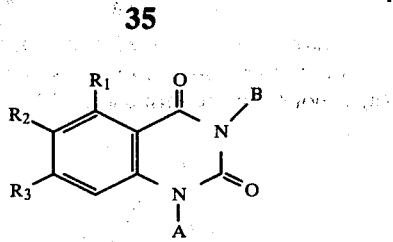

wherein
$R_1$ and $R_3$ independently represent (lower)alkyl;
$R_2$ represents (lower)alkoxycarbonyl;
B represents a (lower)alkyl, phenyl or phenyl substituted by one or two members selected from the group consisting of halogen atoms, (lower)alkyl, (lower)alkoxy, di(lower)alkylamino, methylenedioxy, trifluoromethyl, and nitro; and
A represents a member selected from the group consisting of (a) a hydrogen atom, (b) (lower)alkyl, (c) carboxy(lower)alkyl, (d) (lower)alkoxycarbonyl(lower)alkyl, (e) hydroxy(lower)alkyl, (f) benzyl, (g) benzyl substituted by (1) nitro or (2) (lower)alkoxy, (h) pyridylmethyl, (i) disubstituted-amino (lower)alkyl substituted by (1) two (lower)alkyl or (2) one (lower)alkyl and one of benzyl, tetramethylene, pentamethylene, pentamethylene substituted by (lower)alkyl, hexamethylene or heptamethylene, said methylene forming a heterocycle together with the nitrogen atom of the amino (lower)alkyl, (j) (lower)alkyl bearing a piperidine or pyrrolidine ring, the nitrogen atom of which is substituted by a (lower)alkyl, (k) a moiety of the formula

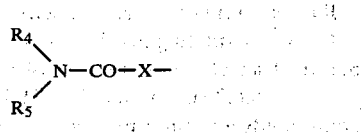

wherein X represents (lower)alkylene, $R_4$ represents a hydrogen atom or (lower)alkyl, $R_5$ represents a hydrogen atom, (lower)alkyl, di(lower)alkylamino(lower)alkyl, benzyl, piperidino(lower)alkyl, morpholino(lower)alkyl, (1-piperazinyl)(lower)alkyl, (4-(lower)acyl-1-piperazinyl)(lower)alkyl, or (4-carbamoyl-1-piperazinyl)(lower)alkyl, the carbamoyl of which may be N-mono- or disubstituted by (lower)alkyl or phenyl, and $R_4$ and $R_5$ can form together with the nitrogen atom a piperidine or 4-(lower)alkylpiperazine ring, (1) a moiety of the formula

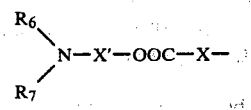

wherein X' and X represent independently (lower)alkylene, $R_6$ represents (lower)alkyl, $R_7$ represents (lower)alkyl, benzyl, piperidino(lower)alkyl, or morpholino(lower)alkyl, and $R_6$ and $R_7$ can form together with the nitrogen atom a piperidine ring, (m) a moiety of the formula

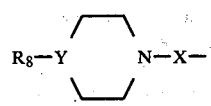

wherein X represents (lower)alkylene, Y represents a nitrogen atom or methine, $R_8$ represents a hydrogen atom, (lower)alkyl, phenyl, phenyl(lower)alkyl, or phenyl(lower)alkene, the phenyl groups of which may be mono- or disubstituted by a chlorine atom, methoxy, benzoyl, benzoyl substituted by a halogen atom, nitro or methoxy, phenylacetyl, benzyloxycarbonyl, cinnamoyl, thenoyl, furoyl, or N-phenylcarbamoyl, provided that when Y is a methine $R_8$ is not hydrogen nor alkyl, and (n) a moiety of the formula

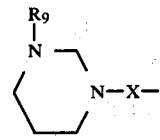

wherein X represents (lower)alkylene, and $R_9$ represents phenyl or benzyl;
or an acid addition salt thereof.

* * * * *